(12) United States Patent
Piccariello et al.

(10) Patent No.: US 7,163,918 B2
(45) Date of Patent: Jan. 16, 2007

(54) IODOTHYRONINE COMPOSITIONS

(75) Inventors: Thomas Piccariello, Blacksburg, VA (US); Lawrence Peter Olon, Bristol, TN (US); Alex Saunders Goldstein, Blacksburg, VA (US); James Scott Moncrief, Christiansburg, VA (US); Nancy Johnston Boerth, Blacksburg, VA (US)

(73) Assignee: New River Pharmaceuticals Inc., Radford, VA (US)

( * ) Notice: Subject to any disclaimer, the term of this patent is extended or adjusted under 35 U.S.C. 154(b) by 452 days.

(21) Appl. No.: 10/136,433

(22) Filed: May 2, 2002

(65) Prior Publication Data

US 2004/0087483 A1 May 6, 2004

Related U.S. Application Data

(63) Continuation-in-part of application No. 09/933,708, filed on Aug. 22, 2001, and a continuation-in-part of application No. 09/642,820, filed on Aug. 22, 2000, now Pat. No. 6,716,452.

(60) Provisional application No. 60/248,607, filed on Nov. 16, 2000.

(51) Int. Cl.
  *A61K 38/04* (2006.01)
  *A61K 38/05* (2006.01)
  *A61K 38/06* (2006.01)
  *C07K 4/00* (2006.01)
  *C07K 5/087* (2006.01)

(52) U.S. Cl. .......................... 514/5; 530/300; 530/331; 530/345; 562/447

(58) Field of Classification Search ................ 530/300, 530/345, 402, 409, 410; 514/5, 563, 567; 562/447
See application file for complete search history.

(56) References Cited

U.S. PATENT DOCUMENTS

| 3,846,399 A | 11/1974 | Hirschmann et al. ....... 530/342 |
| 3,975,342 A | 8/1976 | Gross .......................... 530/363 |
| 3,983,099 A | 9/1976 | Niswender |
| 3,998,799 A | 12/1976 | Bodor et al. ................. 560/251 |
| 4,040,907 A | 8/1977 | Ullman et al. .............. 435/188 |

(Continued)

FOREIGN PATENT DOCUMENTS

EP 0187547 A2 7/1986

(Continued)

OTHER PUBLICATIONS

Ma et al. Enzymatic Mechanism of Thyroxine Biosynthesis. Journal of the American Chemical Society. 1999, vol. 121, No. 38, pp. 8967-8968.*

(Continued)

*Primary Examiner*—Jeffrey Edwin Russel
(74) *Attorney, Agent, or Firm*—Hunton & Williams LLP

(57) ABSTRACT

The present invention relates to compositions comprising thyroxine (T4) and triiodothyronine (T3). More specifically, the invention relates to thyroxine (T4) and triiodothyronine (T3) compositions that include a peptide carrier and thyroxine (T4) and triiodothyronine (T3) covalently attached to at least one of the N-terminus, the C-terminus, a side chain of the peptide carrier, and/or interspersed within the peptide chain; methods for protecting and administering thyroxine (T4) and triiodothyronine (T3); and methods for treating thyroid disorders.

25 Claims, 11 Drawing Sheets

U.S. PATENT DOCUMENTS

| | | | | |
|---|---|---|---|---|
| 4,242,256 | A | 12/1980 | Sharpe et al. | |
| 4,297,346 | A | 10/1981 | Rips et al. | 514/19 |
| 4,332,784 | A | 6/1982 | Smith et al. | |
| 4,341,865 | A | 7/1982 | Voss | |
| 4,351,760 | A | 9/1982 | Khanna et al. | |
| 4,352,751 | A | 10/1982 | Wieder et al. | |
| 4,356,166 | A | 10/1982 | Peterson et al. | 525/54.1 |
| 4,399,121 | A | 8/1983 | Albarella et al. | 530/363 |
| 4,410,513 | A | 10/1983 | Momany | |
| 4,411,890 | A | 10/1983 | Momany | |
| 4,426,453 | A | 1/1984 | Cree et al. | |
| 4,426,455 | A | 1/1984 | Tovey et al. | |
| 4,427,660 | A | 1/1984 | Schiffman et al. | 514/18 |
| 4,457,907 | A | 7/1984 | Porter | 424/10.3 |
| 4,476,228 | A | 10/1984 | Huchzermeier et al. | |
| 4,476,229 | A | 10/1984 | Fino et al. | |
| 4,489,165 | A * | 12/1984 | Wagner et al. | 436/500 |
| 4,552,864 | A | 11/1985 | Antoni et al. | 514/15 |
| 4,650,675 | A | 3/1987 | Borel et al. | 424/179.1 |
| 4,650,750 | A | 3/1987 | Giese | |
| 4,709,016 | A | 11/1987 | Giese | |
| 4,711,855 | A | 12/1987 | Feinberg | |
| 4,719,182 | A | 1/1988 | Burdick et al. | |
| 4,741,897 | A | 5/1988 | Andrews et al. | |
| 4,801,504 | A * | 1/1989 | Burdick et al. | 428/403 |
| 4,801,575 | A | 1/1989 | Pardridge | 514/4 |
| 4,814,484 | A | 3/1989 | Wissmann et al. | |
| 4,820,860 | A | 4/1989 | Wissmann et al. | |
| 4,829,070 | A | 5/1989 | Bodor | |
| 4,863,735 | A | 9/1989 | Kohn et al. | 424/422 |
| 4,902,505 | A | 2/1990 | Pardridge et al. | 424/85.7 |
| 4,960,790 | A | 10/1990 | Stella et al. | 514/449 |
| 4,976,962 | A | 12/1990 | Bichon et al. | 424/424 |
| 5,073,641 | A | 12/1991 | Bundgaard et al. | 560/56 |
| 5,087,616 | A | 2/1992 | Myers et al. | 514/21 |
| 5,120,859 | A | 6/1992 | Webb | |
| 5,169,933 | A | 12/1992 | Anderson et al. | 530/391.3 |
| 5,183,883 | A | 2/1993 | Tanaka et al. | 536/6.4 |
| 5,196,349 | A | 3/1993 | Piran et al. | |
| 5,219,564 | A | 6/1993 | Zalipsky et al. | 424/78.17 |
| 5,238,714 | A | 8/1993 | Wallace et al. | 427/213.3 |
| 5,298,491 | A | 3/1994 | Chauveau et al. | |
| 5,324,522 | A | 6/1994 | Krenning et al. | |
| 5,360,819 | A | 11/1994 | Giese | |
| 5,362,831 | A | 11/1994 | Mongelli et al. | 526/304 |
| 5,378,712 | A | 1/1995 | Alig et al. | |
| 5,516,931 | A | 5/1996 | Giese et al. | |
| 5,534,496 | A | 7/1996 | Lee et al. | 514/17 |
| 5,545,658 | A | 8/1996 | Alig et al. | |
| 5,602,273 | A | 2/1997 | Giese et al. | |
| 5,604,104 | A | 2/1997 | Giese et al. | |
| 5,658,855 | A | 8/1997 | Nalewaja et al. | |
| 5,670,477 | A | 9/1997 | Poduslo et al. | 514/2 |
| 5,670,515 | A | 9/1997 | Alig et al. | |
| 5,691,456 | A * | 11/1997 | Adamczyk et al. | 530/405 |
| 5,698,517 | A | 12/1997 | Bhagavan et al. | |
| 5,747,522 | A | 5/1998 | Alig et al. | |
| 5,762,909 | A | 6/1998 | Uzgiris | 424/9.34 |
| 5,767,227 | A | 6/1998 | Latham et al. | 530/324 |
| 5,811,389 | A | 9/1998 | Bannwarth et al. | |
| 5,843,634 | A * | 12/1998 | Brate et al. | 435/4 |
| 5,846,743 | A | 12/1998 | Janmey et al. | 435/7.8 |
| 5,851,536 | A | 12/1998 | Yager et al. | 424/400 |
| 5,856,359 | A * | 1/1999 | Fischer et al. | 514/567 |
| 5,882,645 | A | 3/1999 | Toth et al. | 424/194.1 |
| 5,891,459 | A | 4/1999 | Cooke et al. | 424/439 |
| 5,898,033 | A | 4/1999 | Swadesh et al. | 514/224.2 |
| 5,910,569 | A | 6/1999 | Latham et al. | 530/324 |
| 5,948,750 | A | 9/1999 | Garsky et al. | 514/2 |
| 5,952,294 | A | 9/1999 | Lazo et al. | 514/2 |
| 5,977,163 | A | 11/1999 | Li et al. | 514/449 |
| 6,005,004 | A | 12/1999 | Katz et al. | 514/549 |
| 6,030,941 | A | 2/2000 | Summerton et al. | 514/2 |
| 6,043,230 | A | 3/2000 | Arimilli et al. | 514/81 |
| 6,048,736 | A | 4/2000 | Kosak | 436/536 |
| 6,074,659 | A | 6/2000 | Kunz et al. | 424/423 |
| 6,093,391 | A | 7/2000 | Kabanov et al. | 424/85.1 |
| 6,306,993 | B1 | 10/2001 | Rothbard et al. | 526/304 |
| 6,309,633 | B1 | 10/2001 | Ekwuribe et al. | 424/85.1 |
| 6,342,225 | B1 * | 1/2002 | Jones et al. | 424/193.1 |
| 6,458,842 | B1 | 10/2002 | Dickinson et al. | 514/567 |
| 6,555,581 | B1 | 4/2003 | Franz et al. | |
| 6,555,582 | B1 | 4/2003 | Schwartz et al. | |
| 6,558,695 | B1 | 5/2003 | Luo et al. | |
| 6,565,879 | B1 | 5/2003 | Luo et al. | |
| 6,632,164 | B1 | 10/2003 | Warburton-Pitt | |
| 6,818,659 | B1 | 11/2004 | Rajopadhye | |
| 2001/0031873 | A1 | 10/2001 | Greenwald et al. | 546/290 |
| 2001/0038862 | A1 | 11/2001 | Luo et al. | |
| 2002/0098999 | A1 | 7/2002 | Gallop et al. | 514/1 |
| 2002/0151526 | A1 | 10/2002 | Gallop et al. | 514/143 |
| 2002/0151529 | A1 | 10/2002 | Cundy et al. | 514/169 |
| 2003/0050344 | A1 | 3/2003 | Garavani et al. | |
| 2003/0147943 | A1 | 8/2003 | Luo et al. | |
| 2004/0087603 | A1 | 5/2004 | Rajopadhye | |
| 2004/0097589 | A1 | 5/2004 | Yi-Lin et al. | |
| 2004/0202719 | A1 | 10/2004 | Zion et al. | |
| 2004/0219218 | A1 | 11/2004 | Martino et al. | |
| 2005/0239217 | A1 | 10/2005 | Graham et al. | |
| 2005/0282872 | A1 | 12/2005 | Hangeland et al. | |

FOREIGN PATENT DOCUMENTS

| | | |
|---|---|---|
| EP | 0 442 372 | 8/1991 |
| EP | 0 457 701 | 11/1991 |
| EP | 0 467 177 | 1/1992 |
| EP | 0 838 472 | 4/1998 |
| EP | 0 982 399 | 3/2000 |
| EP | 1 291 021 | 3/2003 |
| EP | 1 398 024 | 3/2004 |
| EP | 1 433 478 | 6/2004 |
| JP | 58-59954 | 4/1983 |
| WO | WO 95/12605 | 5/1995 |
| WO | WO 95/14033 A1 | 5/1995 |
| WO | WO 96/12499 | 5/1996 |
| WO | WO 96/40202 | 12/1996 |
| WO | WO 97/36616 | 10/1997 |
| WO | WO 98/04277 | 2/1998 |
| WO | WO 99/49901 | 10/1999 |
| WO | WO 00/39077 | 6/2000 |
| WO | WO 01/30749 | 5/2001 |
| WO | WO 01/30802 | 5/2001 |
| WO | WO 02/34237 A1 | 5/2002 |
| WO | WO 02/066017 A1 | 8/2002 |
| WO | WO 03/013441 A2 | 2/2003 |
| WO | WO 2004/007430 | 1/2004 |
| WO | WO 2004/019953 | 3/2004 |
| WO | WO 2004/041208 A2 | 5/2004 |
| WO | WO 2005/040202 | 5/2005 |

OTHER PUBLICATIONS

Orten, James M. et al., "Thyroxine," *Human Biochemistry*, 9th Ed., C.V. Mosby Company, St. Louis,pp. 401-405 (1975).

Li, Chun, et al., "Complete Regression of Well-Established Tumors Using a Novel Water-Soluble Poly(L-Glutamic Acid)-Paclitaxel Conjugate," *Cancer Res*, 58:2404-2409 (1998).

Kramer, Werner et al., "Intestinal Absorption of Peptides by Coupling to Bile Acids," *The Journal of Biochemistry*, 269(14):10621-10627 (1994).

Rawitch, Allen B., et al., "The Isolation of Identical Thyroxine Containing Amino Acid Sequences from Bovine, Ovine and Porcine Thyroglobulins," *Biochemical and Biophysical Research Communications*, 118(2):423-429 (1984).

Marriq, Claudine, et al., "Amino Acid Sequence of the Unique 3,5,3'-Triiodothyronine-Containing Sequence from Porcine Thyroglobulin," *Biochemical and Biophysical Research Communications*, 112(1):206-213 (1983).

Sawada, Kyoko, et al., "Recognition of L-Amino Acid Ester Compounds by Rat Peptide Transporters PEPT1 and PEPT2," *Journal of Pharmacology and Experimental Therapeutics*, 291(2):705-709 (1999).

De Vrueh, Remco L.A., et al, "Transport of L-Valine-Acyclovir Via the Oligopeptide Transporter in the Human Intestinal Cell Line, Caco-2," *Journal of Pharmacology and Experimental Therapeutics*, 286(2):1166-1170 (1988).

Guo, Ailan, et al., "Interactions of a Nonpeptidic Drug, Valacyclovir, with the Human Intestinal Peptide Transporter (hPEPT1) Expressed in a Mammalian Cell Line," *Journal of Pharmacology and Experimental Therapeutics*, 289(1):448-454 (1999).

Burnette, Thimysta C., et al., "Metabolic Disposition of the Acyclovir Prodrug Valaciclovir in the Rat," *Drug Metabolism and Disposition*, 22(1):60-64 (1994).

Aggarwal, et al., "Synthesis and Biological Evaluation of Prodrugs of Zidovudine," *J. Med. Chem.*, 33(5):1505-1511 (1990).

Zunino, Franco, et al., "Comparison of Antitumor Effects of Daunorubicin Covalently Linked to Poly-L-Amino Acid Carriers," *European Journal of Cancer & Clinical Oncology*, 20(3):121-125 (1984).

Havranova, Marie et al., "A High-Molecular Mass Derivative of Trypsin-Kallikrein Inhibitor for Potential Medical Use, II," *Hoppe-Seyler's Z. Physiol. Chem.*, 363:295-303 (1982).

Ryser, Hugues J.P., et al., "Conjugation of Methotrexate to Poly (L-lysine) Increases Drug Transport and Overcomes Drug Resistance in Cultured Cells," *Proc. Natl. Acad. Sci. USA*, 75(8):3867-3870 (1978).

Han, Hyo-Kyung, et al., "Targeted Prodrug Design to Optimize Drug Delivery," *AAPS PharmSci*, 2(1): Article 6 (2000).

Tamai, I., et al., "Improvement of L-dopa Absorption by Dipeptidyl Derivation, Utilizing Peptide Transporter PepT1," *J. Pharma. Sci.*, 87(12):1542-1546 (1988), Abstract.

Oh, D.M., et al., "Drug Transport and Targeting. Intestinal Transport," *Pharma Biotechnol*, 12:59-88 (1999), Abstract.

Balimane, P., et al., "Effect of Ionization on the Variable Uptake of Valacyclovir via the Human Intestine Peptide Transporter (hPepT1) in CHP cells," *Biopharm Drug Dispos*, 21(5):165-174 (2000), Abstract.

Knutter, I, et al., "A Novel Inhibitor of the Mammalian Peptide Transporter PEPT1," *Biochemistry*, 40(14):4454-4458 (2001), Abstract.

Shen, H., et al., "Developmental Expression of PEPT 1 and PEPT2 in Rat Small Intestine, Colon, and Kidney," *Pediatr Res*, 49(6):789-795 (2001), Abstract.

Friedrichsen, G.M., et al., "Model Prodrugs Designed for the Intestinal Peptide Transporter. A Synthetic Approach for Coupling of Hydroxy-Containing Compounds to Dipeptides," *Eur J Pharm Sci*, 14(1):13-19 (2001, Abstract.

Han H., et al., "5'-Amino Acid Esters of Antiviral Nucleosides, Acyclovir, and AZT and Absorbed by the Intestinal PEPT1 Peotide Transporter," *Pharm Res*, 15(8):1154-1159 (1998), Abstract.

Balimane, P.V., et al., "Direct Evidence for Peptide Transporter (PepT1)-Mediated Uptake of a Nonpeptide Prodrug, Valacyclovir," *Biochem Biophys Res Commun*, 250(2):246-251 (1998), Abstract.

Han, H.K., et al., "Cellular Uptake Mechanism of Amino Acid Ester prodrugs in Caco-2hPEPT1 Cells Overexpressing a Human Peptide Transporter," *Pharm Res*, 15(9):1382-1386 (1998), Abstract.

Shiraga, T., et al., "Cellular and Molecular Mechanisms of Dietary Regulation on Rat Intestinal H+/Peptide Transporter PepT1," *Gastroenterology*, 116(2):354-362 (1999), Abstract.

Amidon, G.L., et al., "5'-Amino Acid Esters of Antiviral Nucleosides, Acyclovir, and AZT are Absorbed by the Intestinal PEPT1 Peptide Transporter," *Pharm Res*, 16(2):175 (1999), Abstract.

Leibach, F.H, et al., "Peptide Transporters in the Intestine and the Kidney," *Annu Rev Nutri*, 16:99-119 (1996), Abstract.

Herrera-Ruiz, D., et al., "Spatial Expression Patterns of Peptide Transporters in the Human and Rat Gastrointestinal Tracts, Caco-2 in vitro Cell Culture Model, and Multiple Human Tissues," *AAPS PharmSci*, 3(1): E9 (2001), Abstract.

Toth, Istvan, "A Novel Chemical Approach to Drug Delivery: Lipidic Amino Acid Conjugates," *Journal of Drug Targeting*, 2:217-239 (1994).

Negishi, Naoki, et al., "Coupling of Naltrexone to Biodegradable Poly (α-Amino Acids)," *Pharmaceutical Research*, 4(4):305-310 (1987).

Zunino, Franco, et al., "Anti-Tumor Activity of Daunorubicin Linked to Poly-L-Aspartic Acid," *International Journal of Cancer*, 30:465-470 (1982).

Schmidt, Brigitte F., et al., "Peptide-Linked 1,3-Dialkyl-3-acyltriazenes: Gastrin Receptor Directed Antineoplastic Alkylating Agents," *Journal of Medicinal Chemistry*, 37(22):3812-3817 (1994).

Nishida, Koyo, et al., "Pharmacokinetic Analysis of *in Vivo* Metabolism of Amino Acid or Dipeptide Conjugates of Salicylic Acid in Rabbit Intestinal Microorganisms," *Pharmaceutical Research*, 11(1):160-164 (1994).

Kawai, Tohru, et al., "Direct Polymerization of *N*-Carboxy Anhydride of L-Glutamic Acid," *Makromol. Chem.*, 182:2127-2137 (1981).

Canaris, G., "The Colorado Thyroid Disease Prevalance Study," Archives Internal Medicine Articles and Abstracts, vol. 160, No. 4 (2000).

Bunevicius, R., "Effects of Thyroxine as Compared with Thyroxine Plus Triiodothyronine in Patients with Hypothyroidism," *The New England Journal of Medicine*, vol. 340, No. 6 (1999).

Toft, A., "Thyroid Hormone Replacement—One Hormone or Two?," *The New England Journal of Medicine*, vol. 340, No. 6 (1999).

Pade, V., et al., "Link Between Drug Absorption Solubility and Permeability Measurements in Caco-2 Cells," *Journal of Pharmaceutical Sciences*, vol. 87, No. 12 (1998).

Oh, D., et al., "Estimating the Fraction Dose Absorbed from Suspensions of Poorly Soluble Compounds in Humans: A Mathematical Model," *Pharmaceutical Research*, vol. 10, No. 2 (1993).

Amidon, G., et al., "A Theoretical Basis for a Biopharmaceutic Drug Classification: The Correlation of *in Vitro* Drug Product Dissolution and *in Vivo* Bioavailability," *Pharmaceutical Research*, vol. 12, No. 3 (1995).

International Search Report, dated Sep. 3, 2003.

Supplementary Partial European Search Report dated Apr. 7, 2005, included in International Search Report, dated May 6, 2005.

Ma, Y. et al. Enzymatic Mechanism of Thyroxine Biosynthesis, Identification of the "Lost Three-Carbon Fragment," J. Am. Chem. Soc. 1999, vol. 121, No. 38, p. 8967-8968.

Dumond, J., Boggetto, N., Schramm, H., Schramm, W., Takahasi, M., Reboud-Ravaux, M., Thyroxine-derivatives of lipopeptides: bifunctional dimerization inhibitors of human immunodeficiency virus-1 protease, Biochemical Pharmacology, 65 (7), pp. 1097-1102 (2003).

Ganellin, R., Bishop. P., Bambal, R. Chan. S., Law, J., Marabout, B., Luthra, M., Moore, A., Peschard, O., Bourgeat, P., Rose, C., Vargas, F., Schwartz, J., Inhibitors of Tripeptidyl Peptidase II. 2. Generation of the First Novel Lead Inhibitor of Cholecystokinin-8-Inactivating Peptidase: A Strategy for the Design of Peptidase Inhibitors; Journal of Medicinal Chemistry 43(4), pp. 664-674 (2000).

Tabachnick, M., Hao, Y., Korcek, L., Effect of peptide derivatives of thyroxine on the binding of [125I]-thyroxine to purified human thyroxine-binding globulin; Endocrinology 89(2), pp. 606-609 (1971).

Shiba; T., Cahnmann, H., Model reactions for the biosynthesis of thhyroxine. IX. Synthesis of peptides of L-thyroxine; Journal of Organic Chemistry 29(10), pp. 3063-3065 (1964).

Gaddum, J.H., Quantitative observations on thyroxine and allied substances. II. Effects on the oxygen consumption of rats, Journal of Physiology vol. 68; pp. 383-405 (1930).

Results of Professional Search 1 (Not dated).

Results of Professional Search 2 (Not dated).
Results of Professional Search 3 (Not dated).
The American Thyroid Association, "Thyroid Hormone Treatment", Retrieved from the Internet on Apr. 2005, URL:<//http://www.thyroid.org/patients/brochures/HormoneTreatment_brochure.pdf.
Food and Drug Administration, "Food and Drug Administration Notice Regarding Levothyroxine Sodium", Retrieved from the Internet on Mar. 31, 2006, URL:<//http://thyroid.about.com/od/thyrioddrugstreatments/l/blfdarpt.htm.
MedlinePlus®, "Drug Information: Liothyronine", Retrieved from the Internet on Mar. 31, 2006, URL:<//http://www.nlm.nih.go/medlineplus/print/druginfo/medmaster/a682462.html.

* cited by examiner

Acid Drug/N-Terminus Scheme

R'=Radical moiety attached to acid functionality on drug
R=Side chain of amino acid or peptide
HOBt=Hydroxybenzotriazole
DIPC=Diisopropylcarbodiimide Amine Drug/C-Terminus scheme R'=Radical moiety attached to acid functionality on drug
R=Side chain of amino acid or peptide
HOBt=Hydroxybenzotriazole
DIPC=Diisopropylcarbodiimide

Amine/Drug Initiation scheme

R=Side chain of amino acid or peptide
R'=Radical moiety attached to amine functionality on drug
NCA=N-carboxyanhydride

Alcohol Drug/N-Terminus Scheme

R' = Radical moiety attached to alcohol functionality on drug
R = Side chain of amino acid or peptide

Alcohol Drug/Glutamic Acid Dimer Preparation and Conjugation Scheme

R'=Radical moiety attached to acid functionality on drug
R=Side chain of amino acid or peptide
OBt=Oxybenzotriazole
NCA=N-Carboxyanhydride Mechanism of Alcohol Drug from Glutamic Acid Dimer Scheme R' = Radical Moiety attached to alcohol functionality on drug
R = Side chain of amino acid or peptide Figure 7: *In situ* Digestion of Polythroid in Intestinal Epithelial Cell Cultures
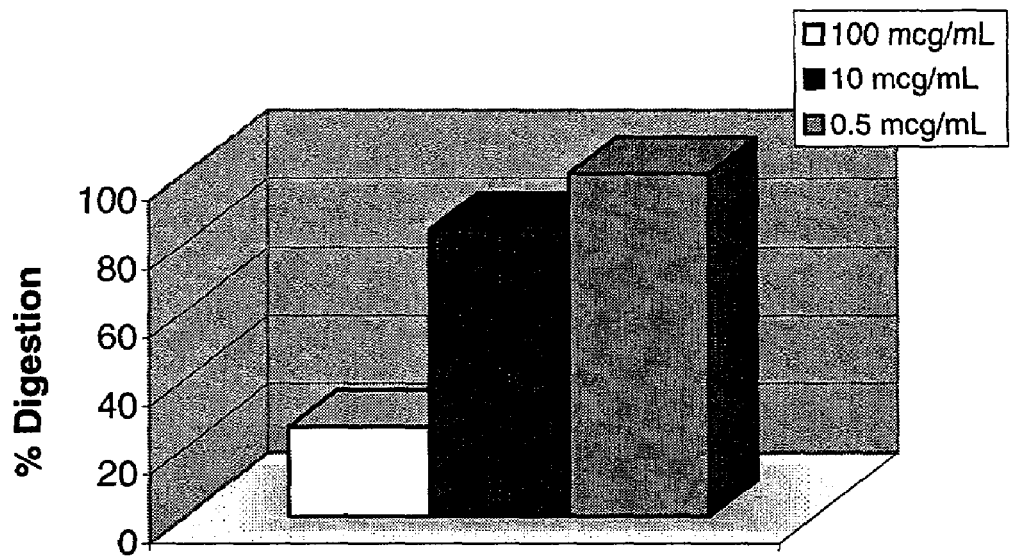
Figure 8: Basolateral T4 Concentrations
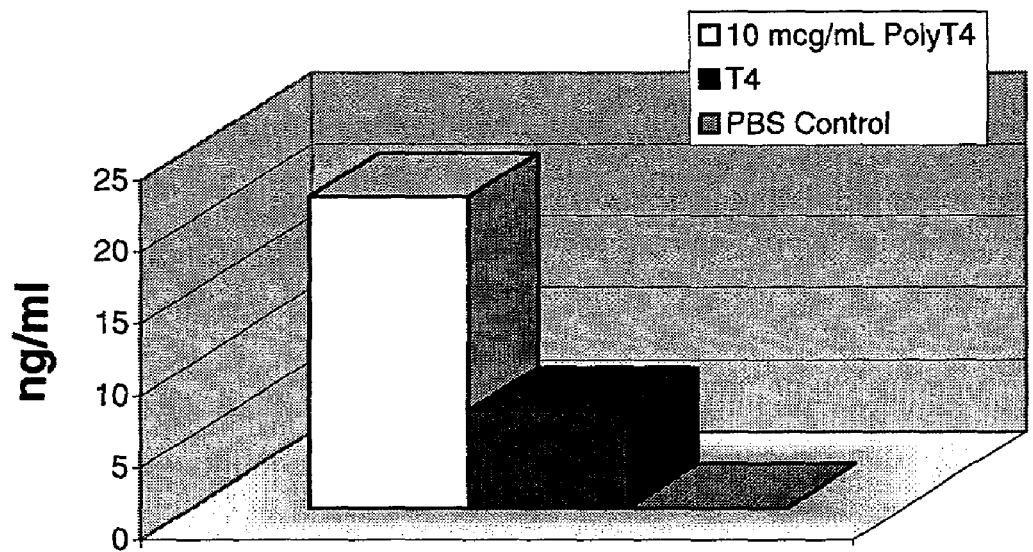

Figure 9: Polythroid concentration
Apical vs. Basolateral
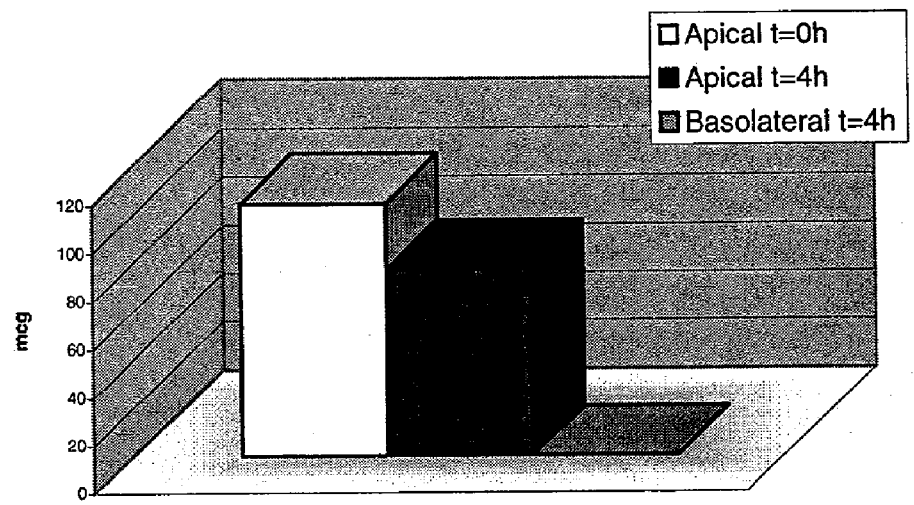
Figure 10: Gastric Simulator vs Intestinal Simulator
T4 Analysis
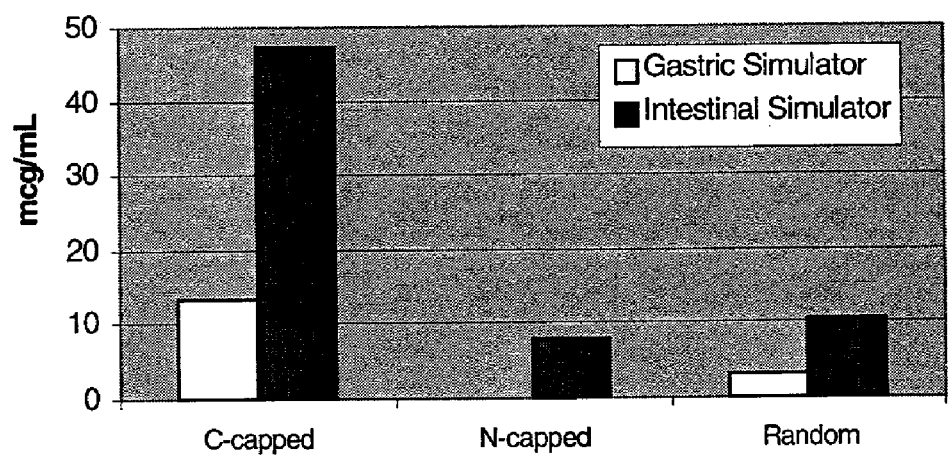

Figure 11: Gastric Simulator vs Intestinal Simulator
T3 Analysis
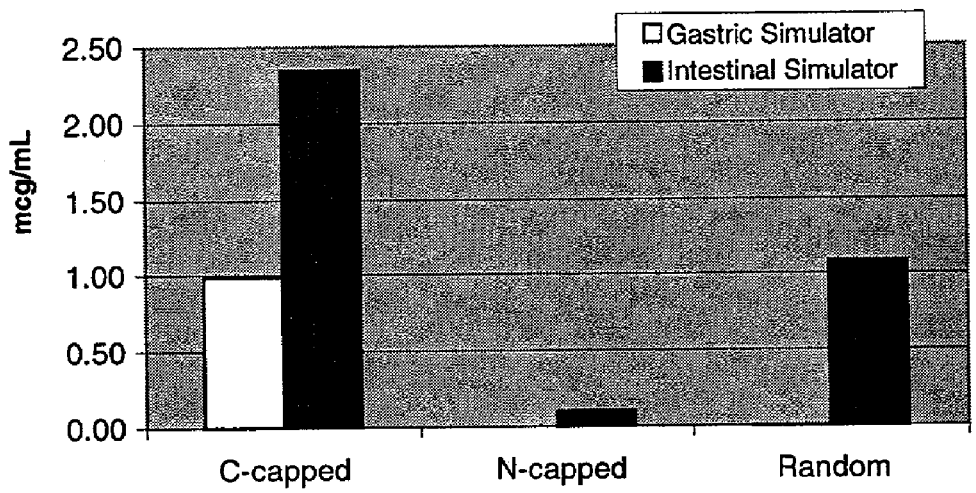
Figure 12: N-capped Trimer vs. T3 Sodium – Total T3 Serum Levels
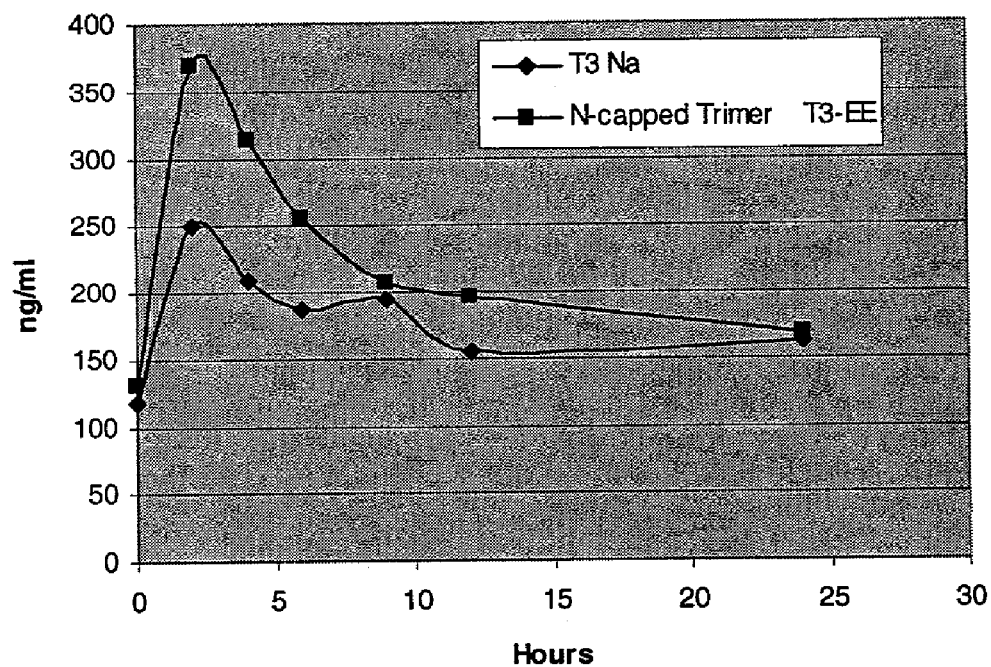

Figure 13: T3 N-Capped Trimer (T3-EE) vs. T3 Sodium Total T3 Serum Deltas
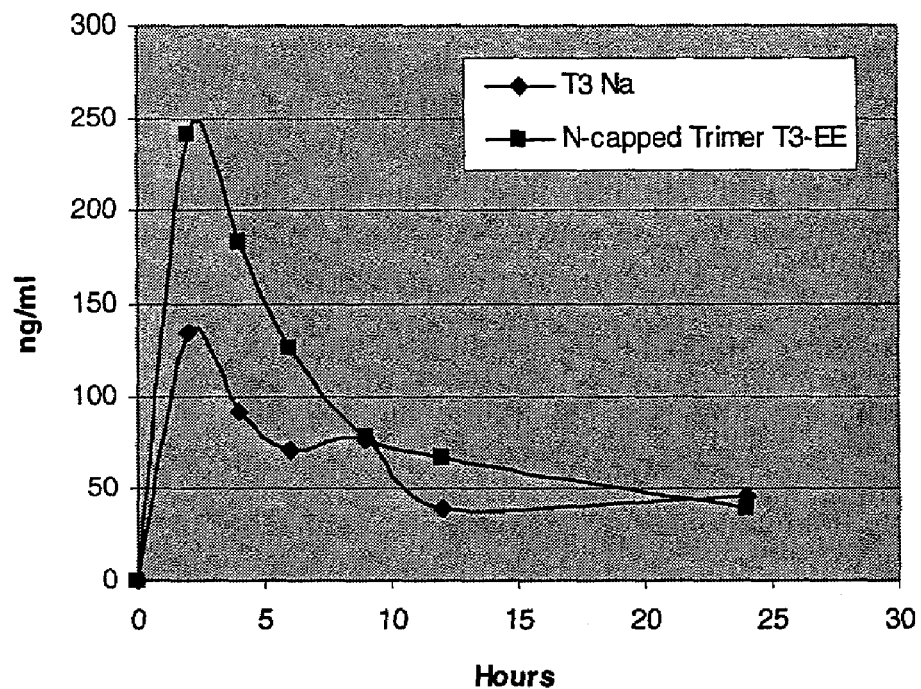
Figure 14. T3 sodium vs. T3 N-capped trimer vs. T3 sodium plus T4 sodium vs. T3 N-capped trimer plus T4 sodium – Total T3 Serum Levels
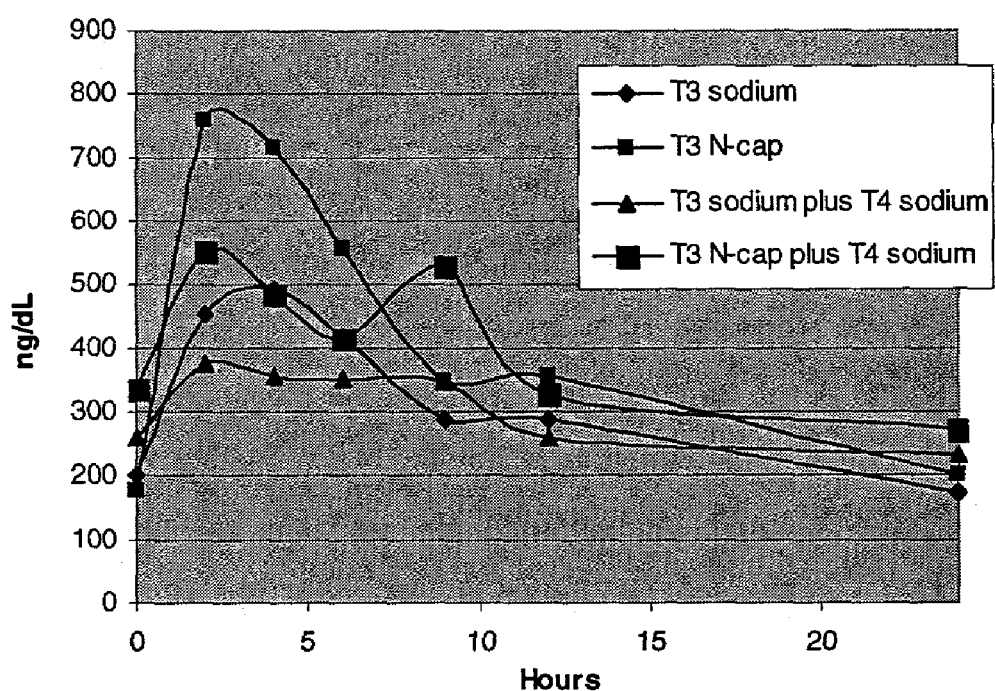

Figure 15: T4 N-capped Trimer (T4-EE) vs. T4 Sodium – Total T4 Serum Levels
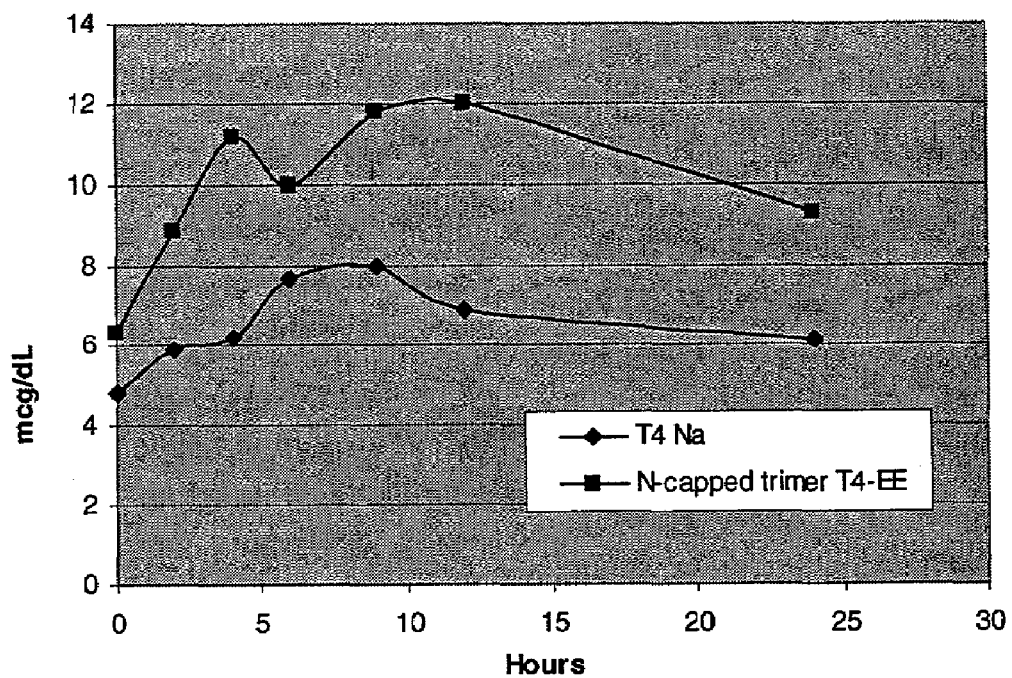
Figure 16: T4 N-Capped Trimer (T4-EE) vs. T4 Sodium Total T4 Serum Deltas
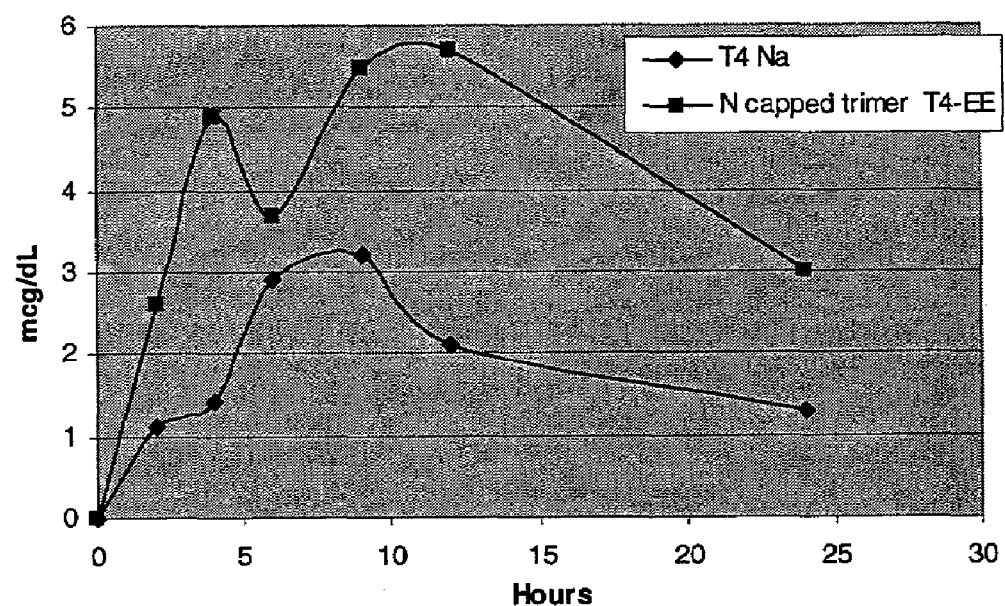

SEQUENCE LISTING

<160> NUMBER OF SEQ ID NOS: 5

<210> SEQ ID NO 1
<211> LENGTH: 5
<212> TYPE: PRT
<213> ORGANISM: Artificial Sequence
<220> FEATURE:

-continued

```
<223> OTHER INFORMATION: Synthetic carrier
<220> FEATURE:
<221> NAME/KEY: MISC_FEATURE
<222> LOCATION: (3)..(3)
<223> OTHER INFORMATION: T3

<400> SEQUENCE: 1

Glu Glu Glu Glu Glu
1               5

<210> SEQ ID NO 2
<211> LENGTH: 9
<212> TYPE: PRT
<213> ORGANISM: Artificial sequence
<220> FEATURE:
<223> OTHER INFORMATION: Synthetic Carrier
<220> FEATURE:
<221> NAME/KEY: MISC_FEATURE
<222> LOCATION: (6)..(6)
<223> OTHER INFORMATION: T3

<400> SEQUENCE: 2

Glu Glu Glu Glu Glu Glu Glu Glu Glu
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic carrier
<220> FEATURE:
<221> NAME/KEY: MISC_FEATURE
<222> LOCATION: (2)..(2)

<400> SEQUENCE: 3

Glu Glu Glu Glu Glu
1               5

<210> SEQ ID NO 4
<211> LENGTH: 19
<212> TYPE: PRT
<213> ORGANISM: Artificial sequence
<220> FEATURE:
<223> OTHER INFORMATION: Synthetic carrier
<220> FEATURE:
<221> NAME/KEY: MISC_FEATURE
<222> LOCATION: (15)..(15)

<400> SEQUENCE: 4

Glu Glu Glu Glu Glu Glu Glu Glu Glu Glu Glu Glu Glu Glu Glu
1               5                   10                  15

Glu Glu Glu

<210> SEQ ID NO 5
<211> LENGTH: 7
<212> TYPE: PRT
<213> ORGANISM: Artificial Sequence
<220> FEATURE:
<223> OTHER INFORMATION: Synthetic carrier
<220> FEATURE:
<221> NAME/KEY: MISC_FEATURE
<222> LOCATION: (3)..(3)
<223> OTHER INFORMATION: T3

<400> SEQUENCE: 5

Glu Glu Glu Glu Glu Glu Glu
1               5
```

IODOTHYRONINE COMPOSITIONS

CROSS REFERENCE TO RELATED APPLICATIONS

This application is a continuation-in-part of U.S. application Ser. No. 09/933,708 filed on Aug. 22, 2001 which is herein expressly incorporated-by-reference which claims benefit under 35 U.S.C. 119(e) of U.S. Provisional Application No. 60/248,607, filed Nov. 16, 2000 and is a continuation-in-part of U.S. application Ser. No. 09/642,820, filed August 22, 2000, now U.S. Pat. No. 6,716,452 which is herein expressly incorporated-by-reference in its entirety.

BACKGROUND OF THE INVENTION (i) Field of the Invention

The present invention relates to compositions comprising an active agent. More specifically, the invention relates to active agent compositions that include a peptide and an active agent covalently attached to at least one of the N-terminus, the C-terminus, a side chain of the peptide, and/or interspersed within the peptide chain. The present invention also relates to methods for protecting and administering active agents and for treating thyroid disorders.

(ii) Description of the Related Art

In the euthyroid state, the thyroid gland is the source of two iodothyronine hormones, thyroxine (T4) and triiodothyronine (T3). Both T4 and T3 play a key role in brain development, and in the growth and development of other organ systems. The iodo-hormones also stimulate the heart, liver, kidney, and skeletal muscle to consume more oxygen, directly and indirectly influence cardiac function, promote the metabolism of cholesterol to bile acids, and enhance the lipolytic response to fat cells.

It has been estimated that the normal thyroid releases molecules of T4 and T3 in a ratio of 5:1 respectively, but other estimates in the order of 10:1 appear in the literature. It has also been reported that 20 percent of circulating T3 is released from the thyroid, while the remaining 80 percent results from the conversion of T4 to T3 by peripheral organs such as the liver. The deiodinase enzyme responsible for this conversion exists as two major isozymes. Type I deiodinase is found predominantly in the liver, kidneys, and thyroid and functions primarily to provide circulating T3, whereas Type II deiodinase acts mainly to supply intracellular T3 to the organs in which it is found, e.g., the brain and the pituitary.

The conversion of T4 to T3 involves a complex cascade of biochemical events which include substrate delivery by the bloodstream, binding and dissociation of T4 with serum proteins, capillary transit time, exposure and binding to and transport through cell membranes, intracellular transport, and the overall activity of the deiodinase enzyme responsible for the conversion. Cofactors and the competing balance between deiodination at the 5' position and the 3' position of T4, in turn, affect the activity of the deiodinase enzyme. Availability of the cofactor glutathione, pH, and the extent of sulfonation all influence this balance. Therefore, treating hypothyroidism with T4 alone may fail to metabolize and provide the required amount of T3 if any steps in the biochemical cascade are disrupted.

Hypothyroidism is the most common disorder of the thyroid and is manifested through the thyroid gland's inability to produce sufficient thyroid hormone. Symptoms associated with hypothyroidism include cold intolerance, lethargy, fatigue, chronic constipation and a variety of hair and skin changes. Although none of these conditions are life threatening, the disease, left untreated, could result in myxedema, coma, or death.

The cause of hypothyroidism in the U.S. is brought about by either autoimmune destruction of the thyroid tissue (Hashimoto's disease), $^{131}$I therapy, or ablative surgery. It is estimated that 8 to 10 million people in the United States have low thyroid gland function, but only about 4 to 5 million hypothyroid cases have been diagnosed and treated. The prevalence of hypothyroidism increases with age, particularly within the female population.

Currently, the most common treatment for hypothyroidism has been the administration of desiccated pig thyroid, levothyroxine sodium (T4), liothyronine sodium (T3), or a combination of T4 and T3. Unfortunately, the available treatments for hypothyroidism have several drawbacks. For instance, the use of desiccated pig thyroid raises concerns regarding its purity and potency due to its source. In addition, the use of T3 has been limited due to safety concerns raised by "spiking." Spiking has also been known to occur with T3 in combination with T4 (sold under the trade name THYROLAR®). Furthermore, the most popular drug T4, which is a prohormone that requires metabolism to T3 in vivo for the drug to be effective, has a short shelf life. Ameliorating T4's inherent instability has been reported. U.S. Pat. No. 5,635,209 claims enhanced stability of T4 preparations through the addition of potassium iodide. U.S. Pat. No. 5,225,204 is directed to improving the stability of levothyroxine sodium. This patent indicates that the stability of the levothyroxine is affected by the presence of some carbohydrate excipients, such as dextrose, starch, sugar, and lactose. This patent claims that stability is achieved through mixing the levothyroxine with a cellulose carrier, with or without the addition of either polyvinyl pyrrolidine (PVP) or a Poloxamer. U.S. Pat. No. 5,955,105 is also directed to providing an improved, stable, solid dosage form of thyroid hormone pharmaceutical preparations. This patent claims pharmaceutical preparations of thyroxine drugs including a water-soluble glucose polymer and a partially soluble or insoluble cellulose polymer to provide the stability. The indicated stability is determined as an absence of potency loss when the preparation is stored at 40 degrees C. and 75 percent relative humidity for six months. U.S. Pat. No. 5,955,105 is hereby incorporated by reference, particularly for its teachings on components and production of pharmaceutical preparations of thyroxine drugs.

The effective delivery of a biologically active agent (active agent) is often critically dependent on the active agent delivery system used. The importance of these systems becomes magnified when patient compliance and active agent stability are taken under consideration. Certainly, T4 would benefit from a formulation that prolongs shelf life. In addition, increasing the absorption of orally administered T4 should also reduce the potential for overdosing and shorten the titration time for patients. As mentioned above, the blunting of the T3 "spike" through a modulated release formulation would markedly improve the safety of that drug. In general, increasing the stability of any active agent, such as prolonging shelf life or survival in the stomach, will assure dosage reproducibility and perhaps even reduce the number of dosages required which could improve patient compliance.

Absorption of an orally administered active agent is often blocked by the harshly acidic stomach milieu, powerful digestive enzymes in the GI tract, permeability of cellular membranes, and transport across lipid bilayers. Incorporating adjuvants such as resorcinol, surfactants, polyethylene glycol (PEG), or bile acids, enhance permeability of cellular membranes. Microencapsulating active agents using protenoid microspheres, liposomes, or polysaccharides have been effective in abating enzyme degradation of the active agent. Enzyme inhibiting adjuvants have also been used to prevent enzyme degradation. Enteric coatings have been used as a protector of pharmaceuticals in the stomach.

Active agent delivery systems also provide the ability to control the release of the active agent. For example, formulating diazepam with a copolymer of glutamic acid and aspartic acid enables a sustained release of the active agent. As another example, copolymers of lactic acid and glutaric acid are used to provide timed release of human growth hormone. A wide range of pharmaceuticals purportedly provide sustained release through microencapsulation of the active agent in amides of dicarboxylic acids, modified amino acids, or thermally condensed amino acids. Slow release rendering additives can also be intermixed with a large array of active agents in tablet formulations.

Each of these technologies imparts enhanced stability and time-release properties to active agent substances. Unfortunately, these technologies suffer from several drawbacks. Incorporation of the active agent is often dependent on diffusion into the microencapsulating matrix, which may not be quantitative and may complicate dosage reproducibility. In addition, encapsulated drugs rely on diffusion out of the matrix, which is highly dependant on the water solubility of the active agent. Conversely, water-soluble microspheres swell by an infinite degree and, unfortunately, may release the active agent in bursts with little active agent available for sustained release. Furthermore, in some technologies, control of the degradation process required for active agent release is unreliable. For example, an enterically coated active agent depends on pH to release the active agent and, therefore, control of the rate of release is difficult to achieve.

It is also important to control the molecular weight, molecular size, and particle size of the active agent delivery system. Variable molecular weights have unpredictable diffusion rates and pharmacokinetics. High molecular weight carriers are digested slowly or late, as in the case of naproxen-linked dextran, which is digested almost exclusively in the colon by bacterial enzymes. High molecular weight microspheres usually have high moisture content which may present a problem with water labile active ingredients, such as T4. Due to the inherent instability of non-covalent bonds, the bond between the active agent and the microsphere will usually not withstand the vigorous conditions used to reduce the composition's particle size.

U.S. application Ser. No. 09/411,238, filed Oct. 4, 1999, now Abandoned, and entitled "Use of Protein Conformation for the Protection and Release of Chemical Compounds," hereby incorporated by reference, is directed to the manipulation of protein conformation in the protection and release of chemical compounds. The invention is based on the formation of higher-order structures that proteins assume under various salt, solvent, and pH conditions so as to protect chemical compounds and/or control the release thereof in vitro or in vivo environments.

There remains a need for compositions that effectively deliver one or more active agents synergistically. There also remains a need for compositions that protect active agents, either during storage or through the stomach. There also remains a need for methods of protecting and controlling the delivery and/or release of active agents. No attempt, heretofore reported by the inventors or elsewhere, have been made to increase the absorption of either T3 or T4 through the intestinal epithelia.

Therefore, the need still exists for a drug delivery system, which enables the use of new molecular compositions which can reduce the technical, regulatory, and financial risks associated with active agents while improving the reproducibility, bioavailability, reliability, and sustained release.

SUMMARY OF THE INVENTION

The invention provides covalent attachment of an iodothyronine active agent(s) to an peptide, hereafter referred to as peptidic iodothyronine compositions. The invention covalently attaches the active agent, which may include, for example, adjuvants, within the peptide in a peptide-linked manner, to the N-terminus, the C-terminus, or to the amino acid side chain of a peptide, also referred to herein as a carrier peptide. In a more preferred embodiment the attachment is without the use of a linker. The carrier peptide itself may also serve as an adjuvant. The invention also provides for at least one iodothyronine active agent that is covalently interspersed within the carrier peptide. In a preferred embodiment, the iodothyronine active agent is covalently attached to the N-terminus or the C-terminus of the carrier peptide or amino acid, hereafter to be referred to as capped iodothyronine compositions. In another preferred embodiment, the iodothyronine active agent is covalently attached directly to the amino acid side chain of the carrier peptide or amino acid, hereafter to be referred to as side chain iodothyronine compositions. In a further preferred embodiment, the iodothyronine active agent is covalently interspersed within the carrier peptide, hereafter to be referred to as interspersed iodothyronine compositions. In another preferred embodiment the polypeptide contains one or more of the 20 naturally occurring amino acids. As used herein, the term "iodothyronine active agent" refers to a compound of formula I

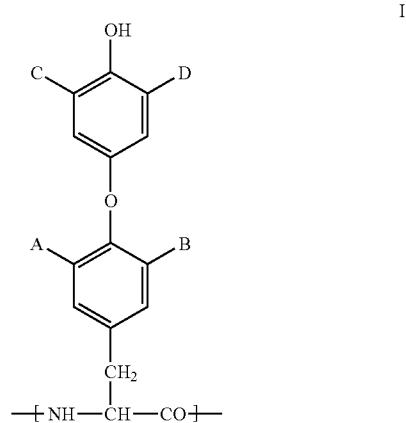

in which A is iodo and B, C and D are independently hydrogen or iodo. In formula I the NH— is attached to a hydrogen and the CO— of formula I is attached to a hydroxyl; i.e., $NH_2$ and COOH, respectively. Preferably, iodothyronine active agents are T3 or T4.

In an embodiment of the present invention, the carrier peptide stabilizes the iodothyronine active agent, during storage, thus extending shelf life of the active agent. In another embodiment, the polypeptide stabilizes the active agent, primarily in the stomach, through conformational protection. In this embodiment, delivery of the active agent is controlled, in part, by the kinetics of unfolding of the carrier peptide. Upon entry into the upper intestinal tract, indigenous enzymes release the active ingredient for absorption by the body by hydrolyzing the peptide bonds of the carrier peptide. This enzymatic action introduces the second phase of the sustained release mechanism. In yet another embodiment of the present invention, the absorption of the iodothyronine active agent is increased by modulated release, targeting active amino acid or peptide transporters, by being covalently attached to one or more amino acids, or a combination thereof.

In the euthyroid or normal state, the thyroid gland secretes both T4 and T3 into the bloodstream; the constant availability of both hormones to target tissues at levels in excess of those possible by peripheral deiodination of T4 alone is essential for optimum health and well being. Thus the invention allows for the mimicry of certain activities of the normal thyroid, namely, the synthesis of a carrier peptide containing both hormones and following proteolysis of the carrier peptide, the release of the two hormones into the bloodstream in approximately the same T4:T3 ratio as secreted by the healthy thyroid gland.

The invention provides compositions comprising a carrier peptide and an iodothyronine active agent covalently attached to the carrier peptide. Preferably, the carrier peptide is (i) an amino acid, (ii) a dipeptide, (iii) a tripeptide, (iv) an oligopeptide, or (v) a polypeptide. The carrier peptide may also be (i) a homopolymer of a naturally occurring amino acids, (ii) a heteropolymer of two or more naturally occurring amino acids, (iii) a homopolymer of a synthetic amino acid, (iv) a heteropolymer of two or more synthetic amino acids, or (v) a heteropolymer of one or more naturally occurring amino acids and one or more synthetic amino acids.

Furthermore, amino acids with reactive side chains (e.g., glutamic acid, lysine, aspartic acid, serine, threonine, and cysteine) can be incorporated for attaching multiple active agents or adjuvants to the same carrier peptide. This is particularly useful if a synergistic effect between two or more active agents is desired. An embodiment of the invention comprises iodothyronine that is peptide linked to the carrier peptide, and an adjuvant that enhances absorption is attached to the side chain of one or more of the amino acids of the carrier peptide.

In one embodiment the amine and carboxylic acid groups of the iodothyronine active agent is covalently interspersed within the peptide chain. In another embodiment the iodothyronine active agent is covalently attached to the N-terminus, the C-terminus, or the side chain of the peptide. In another embodiment the active agent composition may be a combination of the two above embodiments.

The location of attachment depends on the functional group selected for covalent attachment. For instance, the carboxylic acid of iodothyronine is attached to the N-terminus of the carrier peptide as shown in FIG. 1. Alternatively, the carboxylic acid group can be attached to the side chain of an appropriately substituted amino acid such as lysine. The amine functionality of iodothyronine is attached to the C-terminus of the carrier peptide as shown in FIG. 2. In both, the C- and N-terminus examples, one monomeric unit forming a new peptide bond in essence, extends the carrier peptide chain. If both the amine and the carboxylic acid of the iodothyronine are used to attach to the carrier peptide, then a peptide-linked interspersed iodothyronine composition is made. If the alcohol of the iodothyronine is used to attach to the carrier peptide, then the side chain, the C-terminus or the N-terminus is the point of attachment in order to achieve a stable composition, although a carbonyl, or its equivalent may need to be inserted between the alcohol and the peptide functional group.

The peptide-linked interspersed iodothyronine comprises iodothyronine active agents that are directly attached to iodothyronine active agents, or iodothyronine active agents that are not directly attached to iodothyronine active agents, or a combination thereof. In a preferred embodiment, any number of iodothyronine active agents are interspersed within the carrier peptide. In a preferred embodiment of the present invention, iodothyronine active agents directly attached to iodothyronine active agents do not form a linked chain of contiguous iodothyronine active agents that is greater than five contiguous iodothyronine active agents. In a further preferred embodiment, interspersed iodothyronine active agents form a linked chain of contiguous iodothyronine active agents of four or less contiguous iodothyronine active agents.

In another embodiment of the present invention, for modulated delivery or increased bioavailability of the iodothyronine active agents, the preferred length of the peptide is between two and 50, with-lengths between two and 15 being even more preferred. For conformational protection, extended digestion time and sustained release, preferred peptide lengths may be between 8 and 400 amino acids. In a preferred embodiment the peptide length is between two and 10 amino acids, including the iodothyronine active agent. In one preferred embodiment the iodothyronine active agent composition is a trimer, in particular the trimer may be iodothyronine and glutamic acid. In another preferred embodiment the iodothyronine active agent is randomly dispersed in a peptide with a length between eight and 10 amino acids in length including the iodothyronine active agent, in particular the random interspersement may be iodothyronine and glutamic acid.

The invention provides a method for delivering an iodothyronine active agent to a patient, the patient being a human or a non-human animal, comprising administering to the patient a composition comprising a carrier peptide and an iodothyronine active agent covalently attached to the carrier peptide or interspersed within the carrier peptide. The composition can include an adjuvant either covalently attached to or microencapsulated within the carrier peptide. In a preferred embodiment, the adjuvant activates an intestinal transporter, bioadheres to the intestinal mucosa, bioadheres to a cell surface under the intestinal mucosa, or a combination thereof.

The compositions of the invention can be formulated in pharmaceutical compositions by combining the compound with a pharmaceutically acceptable carrier. Examples of such excipients are set forth below.

The iodothyronine active agents may be employed in powder or crystalline form, in liquid solution, or in suspension. It may be administered by a variety of means, including but not limited to: topically, orally and parenterally by injection (intravenously or intramuscularly).

Compositions for injection, one route of delivery, may be prepared in unit dosage form in ampules, or in multidose containers. The injectable compositions may take such forms as suspensions, solutions, or emulsions in oily or aqueous vehicles, and may contain various formulating agents. Alternatively, the active ingredient may be in powder form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Topical applications may be formulated in carriers such as hydrophobic or hydrophilic bases to form ointments, creams, lotions, in aqueous, oleaginous or in dry diluents to form powders.

Oral compositions may take such forms as tablets, capsules, oral suspensions and oral solutions. The oral compositions may utilize carriers such as conventional formulating agents, and may include sustained release properties as well as rapid delivery forms.

The dosage to be administered depends to a large extent upon the condition and size of the subject being treated, the route and frequency of administration.

One embodiment of the methods of administration of the iodothyronine active agents includes oral and parenteral methods, e.g., i.v. infusion, i.v. bolus and i.m. injection.

In a further embodiment of the invention, the composition incorporates a microencapsulating agent. Preferably, the composition of the invention is in the form of an ingestible tablet or capsule, an implantable device, a skin patch, a sublingual preparation, a subcutaneous preparation, an intravenous preparation, an intraperitoneal preparation, an intramuscular preparation or an oral suspension.

The peptidic iodothyronine compositions of the invention have advantages over T4 and T3 alone because the peptidic iodothyronine compositions are a functional surrogate of the naturally occurring thyroglobulin. Specifically, the release of the iodothyronine active agent from the peptide is regulated by alimentary enzymes, thus smoothing the absorption and, perhaps more importantly, obviating T3 spiking.

The methods, compounds and compositions of the present invention provide many important advantages and advances. Compositions of the present invention may be synthetically produced to alleviate the purity and potency concerns associated with the use of desiccated pig thyroid. The methods and compositions of the present invention prevent and/or avoid overdosing (e.g., "spiking"). The stability of the iodothyronine active agents (e.g., prolonging of shelf life, survival in the stomach, etc.) is increased by the present invention. In preferred embodiments, improving stability of the active agents assures dosage reproducibility and/or reduces the number of dosages required. By assuring dosage reproducibility and/or reducing dosage availability, the present invention provides the added advantage of improving patient compliance. The present invention provides time-release properties to the active agents. Providing time-release properties also assures dosage reproducibility and/or reduces the number of dosages required.

As discussed, a preferred embodiment of the present invention provides increased stability of the iodothyronine active agents. In a preferred embodiment, this increased stability is provided without the addition of potassium iodide. In another preferred embodiment, the increased stability is provided without the addition of a carbohydrate excipient(s). In yet another preferred embodiment, the increased stability is achieved without mixing the iodothyronine active agents with a cellulose carrier. In a further embodiment, the increased stability is provided without including a water-soluble glucose polymer and/or a partially soluble or insoluble cellulose polymer.

In a preferred embodiment, the enhanced stability and/or time-release properties provided by the present invention are not dependent upon diffusion of the active agents into a microencapsulating matrix during manufacturing. This provides a further advantage of reliable dosing and batch to batch reproducibility. In another preferred embodiment of the present invention, the iodothyronine active agents need not rely on diffusion out of a matrix (e.g., encapsulated drugs) for enhanced stability and/or time-release properties. This embodiment provides a further advantage of providing the enhanced stability and/or time-release properties without heightened dependence on water solubility of the iodothyronine active agents. In another embodiment, the enhanced stability and/or time-release properties are not controlled by a dissolution process, such as involved in an enterically coated active agent controlled by pH.

Another advantage provided by preferred embodiments of the present invention is the control of iodothyronine active agent delivery system with regard to molecular weight, molecular size, particle size or combinations thereof. The control of these physical characteristics provided by this embodiment enables predictable diffusion rates and pharmacokinetics.

In a preferred embodiment of the present invention, one or more iodothyronine active agents are delivered synergistically. In another embodiment, the compositions of the present invention protect the iodothyronine active agents during storage and/or in passage through the stomach. In a more preferred embodiment, the present invention provides methods for protecting, controlling delivery, or controlling release of active agents, or combinations thereof.

In another preferred embodiment of the invention the solubility of the active agent is enhanced by attachment to the peptide carrier. Enhanced solubility in aqueous solutions, such as those found in the intestinal tract, provide improved bioavailability of the active agent. In another embodiment of the invention the solubility of the active agent composition is enhanced in organic solvents such as, isopropanol and acetone. Enhanced solubility in these solvents allows even dispersion of the active agent in polymer formulations that require certain organic solvents. In a preferred embodiment of the invention, the active agent composition provides enhanced solubility in a solution of about 60% isopropanol and 40% acetone allowing even dispersion of the active agent in pH sensitive polymers such as Eudragit L100. Dispersion of the active agent in these polymers allows protection from dissolution and active agent release in the stomach and affords gradual dissolution and time-release in the intestine. Protecting the composition from degradation by enzymes through the stomach allows the added advantage of providing active agent release through small intestine enzymes.

In a preferred embodiment, absorption of the active agent is enhanced by attachment to glutamic acid or a peptide composed of glutamic acid. The defined active agent-peptide composition may be prepared by solid phase synthesis or other chemical means. Enhancement of absorption may occur through enhanced solubility of the compound and/or through receptor mediated uptake and/or through other mechanisms. The peptide carrier may also serves as an adjuvant to iodothyronine composition's absorption.

As synthetic peptides are included within the scope of the peptidic iodothyronine compositions of the present invention, the purity and chemical properties can be controlled and manipulated. Additionally, the precise chemical structure (i.e., the peptide/iodothyronine active agent ratio and the molecular weight) of the peptidic iodothyronine composition may be under synthetic control, exhibiting a clear advantage over desiccated pig thyroid or purified thyroglobulin.

It is to be understood that both the foregoing general description and the following detailed description are exemplary, but are not restrictive, of the invention.

BRIEF DESCRIPTION OF THE FIGURES

The invention is best understood from the following detailed description when read in connection with the accompanying figures in which:

FIG. 7 illustrates the in situ digestion of Polythroid in intestinal epithelial cell cultures;

FIG. 8 illustrates the improved adsorption of T4 from PolyT4 compared to T4 alone;

FIG. 9. illustrates a decrease in the amount of Polythroid on the apical side over time (4 hours) without intact Polythroid crossing the Caco-2 monolayer;

FIG. 10 illustrates release of T4 by Polythroid digestion in the gastric simulator compared to the intestinal simulator;

FIG. 11 illustrates release of T3 by Polythroid digestion in the gastric simulator compared to the intestinal simulator;

FIG. 12 illustrates the mean total T3 serum concentration curves (AUCs) of T3 sodium salt vs. T3 N-capped trimer (T3-EE) and further demonstrates enhanced T3 absorption from a peptide-active agent composition (T3 N-capped trimer, T3-EE) vs. T3 sodium salt;

FIG. 13 illustrates the mean delta serum concentration curves (Δ from zero hour total T3 level) of T3 sodium salt and T3 N-capped trimer (T3-EE) and further demonstrates enhanced T3 absorption from a peptide-actve agent composition (T3 N-capped trimer, T3-EE) vs. T3 sodium salt;

FIG. 14 illustrates the mean total serum concentration curves of T3 sodium salt vs. T3 N-capped trimer (T3-EE) vs. T3 sodium salt plus T4 sodium salt vs. T3 N-capped trimer (T3-EE) plus T4 sodium salt and further demonstrates the inhibitory affect of T4 sodium salt on T3 absorption and the partial elimination of the negative effect of T4 sodium salt on T3 absorption by a peptide-active agent composition (T3 N-capped trimer, T3-EE);

FIG. 15 illustrates the mean total T4 serum concentration curves (AUCs) of T4 sodium salt vs. T4 N-capped trimer (T4-EE) and further demonstrates enhanced T4 absorption from a peptide-active agent composition (T4 N-capped trimer, T4-EE) vs. T4 sodium salt;

FIG. 16 illustrates the mean delta serum concentration curves (Δ from zero hour total T4 level) of T4 sodium salt and T4 N-capped trimer (T4-EE) and further demonstrates enhanced T4 absorption from a peptide-actve agent composition (T4 N-capped trimer, T4-EE) vs. T4 sodium salt.

DETAILED DESCRIPTION OF PREFERRED EMBODIMENTS

Figure 1:
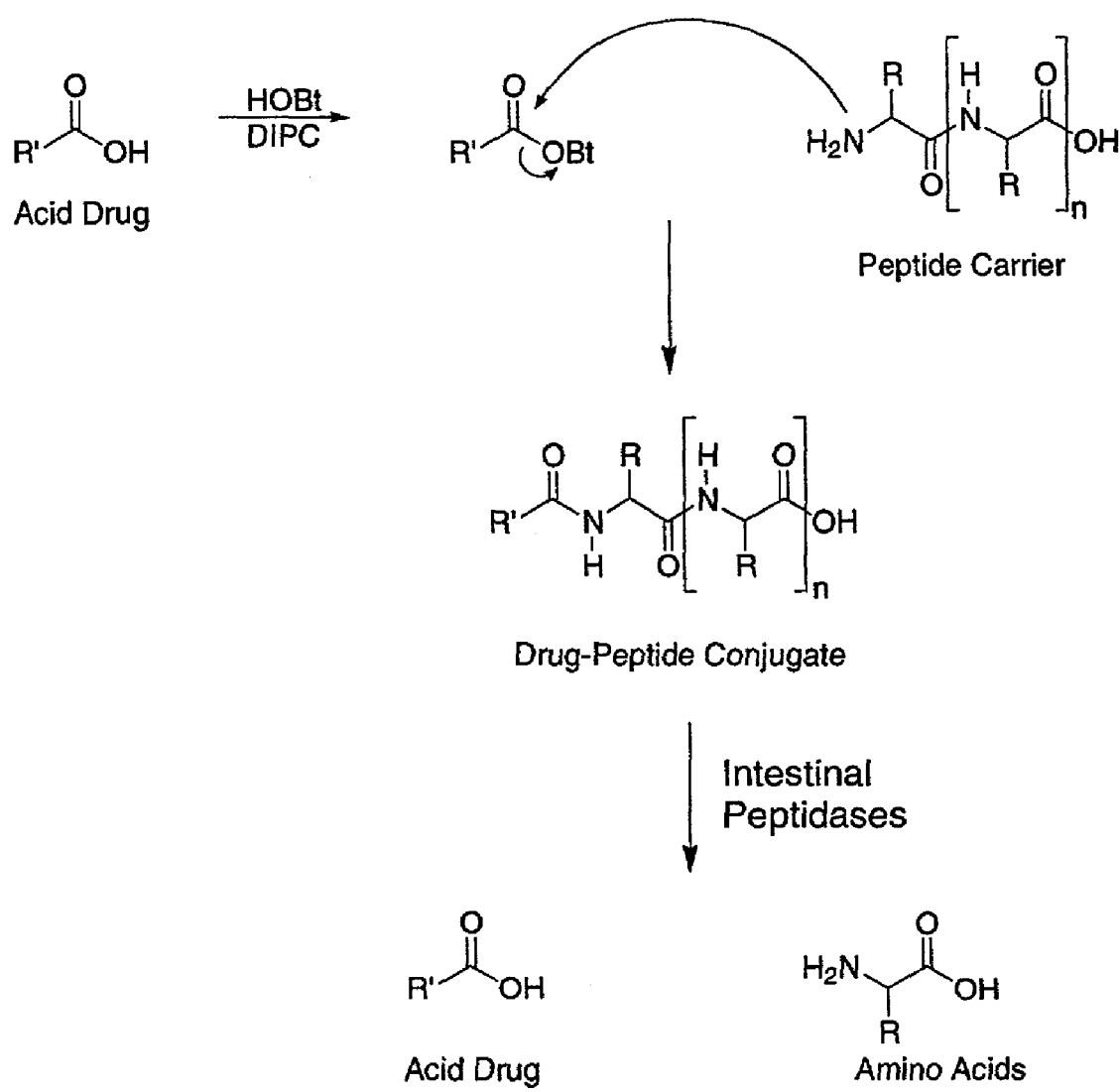
FIG. 1 illustrates a scheme for the attachment of the active agent to the N-terminus of a peptide through the active agent's acid functional group.
Figure 2:
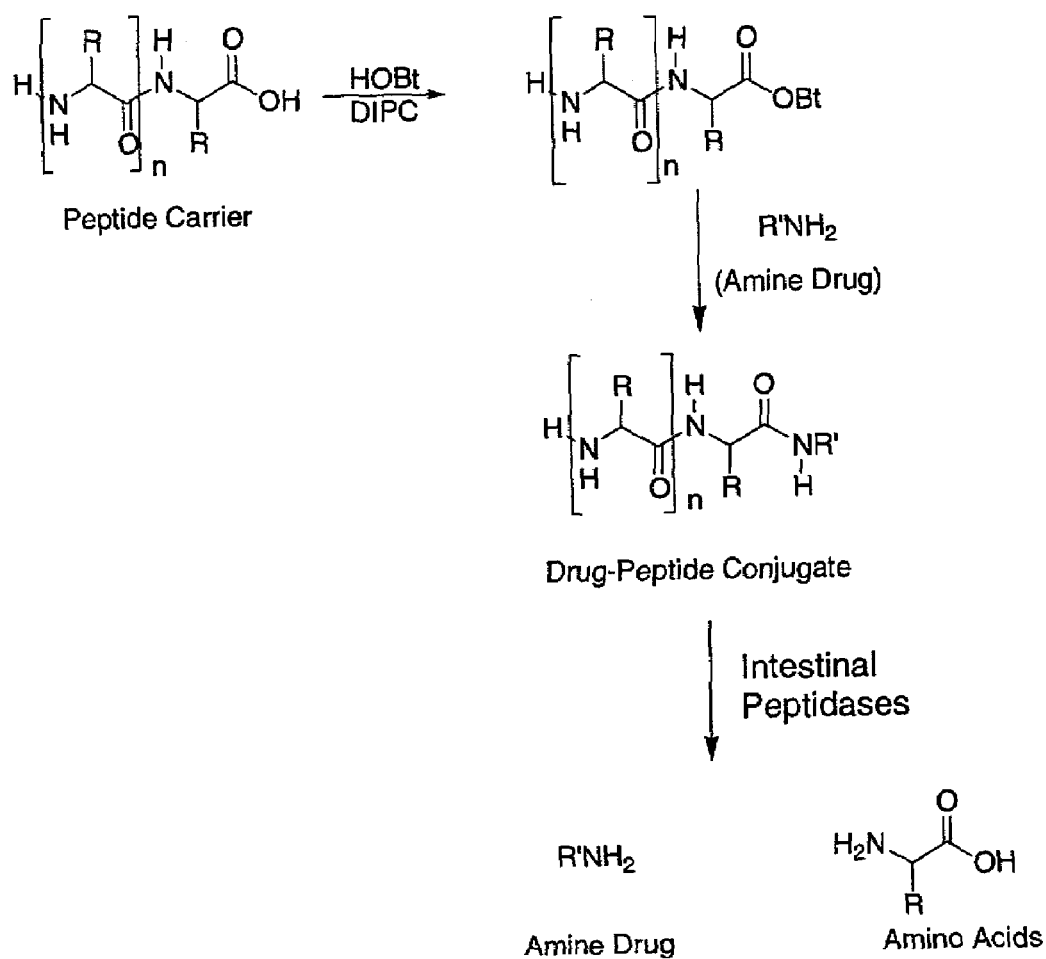
FIG. 2 illustrates a scheme for the attachment of the active agent to the C-terminus of a peptide through the active agent's amine functional group.

Throughout this application the use of "peptide" is meant to include a single amino acid, a dipeptide, a tripeptide, an oligopeptide, a polypeptide, or the carrier peptide. Oligopeptide is meant to include from 2 amino acids to 70 amino acids. Further, at times the invention is described as being an active agent attached to an amino acid, a dipeptide, a tripeptide, an oligopeptide, or polypeptide to illustrate specific embodiments for the active agent conjugate. Preferred lengths of the conjugates and other preferred embodiments are described herein.

The present invention provides several benefits for iodothyronine active agent administration. First, the invention can stabilize the iodothyronine active agent for longer shelf life and prevent digestion in the stomach. The invention also allows targeted delivery of the iodothyronine active agents to specifics sites of action, particularly organ specific. In addition, the pharmacologic effect can be prolonged by delayed release of the iodothyronine active agent. Furthermore, iodothyronine active agents can be combined together or with adjuvants to produce synergistic effects. Additionally, absorption of the active agent in the intestinal tract can be enhanced. Finally, the compositions of the present invention may be formulated for targeted delivery for digestion by intestinal enzymes, intracellular enzymes or blood serum enzymes.

A major portion of the enhanced performance imparted to iodothyronines by the carrier peptide can be explained in terms of the composition's structure. Proteins, oligopeptides, and polypeptides are polymers of amino acids that have primary, secondary, and tertiary structures. The secondary structure of the peptide is the local conformation of the polypeptide chain and consists of helices, pleated sheets, and turns. The peptide's amino acid sequence and the structural constraints on the conformations of the chain determine the spatial arrangement of the molecule. The folding of the secondary structure and the spatial arrangement of the side chains constitute the tertiary structure.

Peptides fold because of the dynamics associated between neighboring atoms on the peptide and solvent molecules. The thermodynamics of peptide folding and unfolding are defined by the free energy of a particular condition of the peptide that relies on a particular model. The process of peptide folding involves, amongst other things, amino acid residues packing into a hydrophobic core. The amino acid side chains inside the peptide core occupy the same volume as they do in amino acid crystals. The folded peptide interior is therefore more like a crystalline solid than an oil drop and so the best model for determining forces contributing to peptide stability is the solid reference state.

The major forces contributing to the thermodynamics of peptide folding are Van der Waals interactions, hydrogen bonds, electrostatic interactions, configurational entropy, and the hydrophobic effect. Considering peptide stability, the hydrophobic effect refers to the energetic consequences of removing apolar groups from the peptide interior and exposing them to water. Comparing the energy of amino acid hydrolysis with peptide unfolding in the solid reference state, the hydrophobic effect is the dominant force. Hydrogen bonds are established during the peptide folding process and intramolecular bonds are formed at the expense of hydrogen bonds with water. Water molecules are "pushed out" of the packed, hydrophobic peptide core. All of these forces combine and contribute to the overall stability of the folded peptide where the degree to which ideal packing occurs determines the degree of relative stability of the peptide The result of maximum packing is to produce a center of residues or hydrophobic core that has maximum shielding from solvent.

Since it is likely that iodothyronine would reside in the hydrophobic core of a peptide, it would require energy to unfold the peptide before the iodothyronine can be released. The unfolding process requires overcoming the hydrophobic effect by hydrating the amino acids or achieving the melting temperature of the peptide. The heat of hydration is a destabilization of a peptide. Typically, the folded state of a peptide is favored by only 5–15 kcal/mole over the unfolded state. Nonetheless, peptide unfolding at neutral pH and at room temperature requires chemical reagents. In fact, partial unfolding of a peptide is often observed prior to the onset of irreversible chemical or conformation processes. Moreover, peptide conformation generally controls the rate and extent of deleterious chemical reactions.

Conformational protection of active agents by peptides depends on the stability of the peptide's folded state and the thermodynamics associated with the agent's decomposition. Conditions necessary for the agent's decomposition should be different than for peptide unfolding.

Selection of the amino acids will depend on the physical properties desired. For instance, if increase in bulk or lipophilicity is desired, then the carrier peptide will be enriched in the amino acids that have bulky, lipophilic side chains. Polar amino acids, on the other hand, can be selected to increase the hydrophilicity of the peptide.

Ionizing amino acids can be selected for pH controlled peptide unfolding. Aspartic acid, glutamic acid, and tyrosine carry a neutral charge in the stomach, but will ionize upon entry into the intestine. Conversely, basic amino acids, such as histidine, lysine, and arginine, ionize in the stomach and are neutral in an alkaline environment.

Other factors such as π—π interactions between aromatic residues, kinking of the peptide chain by addition of proline, disulfide crosslinking, and hydrogen bonding can all be used to select the optimum amino acid sequence for a desired performance parameter. Ordering of the linear sequence can influence how these interactions can be maximized and is important in directing the secondary and tertiary structures of the peptide.

Variable molecular weights of the carrier peptide can have profound effects on the active agent release kinetics. As a result, low molecular weight active agent delivery systems are preferred. An advantage of this invention is that chain length and molecular weight of the peptide can be optimized depending on the level of conformational protection desired. This property can be optimized in concert with the kinetics of the first phase of the release mechanism. Thus, another advantage of this invention is that prolonged release time can be imparted by increasing the molecular weight of the carrier peptide. Another, significant advantage of the invention is that the kinetics of active agent release is substantially controlled by the enzymatic hydrolysis of the key bond between the carrier peptide and the active agent.

The iodothyronine active agent is released from the composition by a pH-dependent unfolding of the carrier peptide or it is released from the composition by an enzyme-catalyzed release. In a further embodiment, the active agent is released from the composition by a combination of a pH-dependent unfolding of the carrier peptide and an enzyme-catalyzed release in a time-dependent manner based on the pharmacokinetics of the enzyme-catalyzed release. The active agent may be released from the composition in a sustained release manner. In another preferred embodiment, the sustained release of the iodothyronine active agent from the composition has zero order pharmacokinetics.

The iodothyronine active agent can be covalently interspersed within the carrier peptide chain in a peptide-linked manner and/or covalently attached to the side chain, the N-terminus or the C-terminus of the carrier peptide. The iodothyronine active agent has an alcohol group and can be covalently attached to the C-terminus or acid containing side chains (e.g., glutamic acid or aspartic acid) of the carrier peptide to produce a new ester linkage between the alcohol of the iodothyronine and the acid side chain of the carrier peptide. The alcohol of the active agent can be covalently attached to the N-terminus or alcohol or amine containing side chains (e.g., serine or lysine) of the carrier peptide with a carbonyl insertion or its equivalent to produce a carbamate or carbonate linkage between the iodothyronine's alcohol group and the carrier peptide. The iodothyronine active agent has an amine group and can be covalently attached to the C-terminus or acid containing side chains (e.g., glutamic acid or aspartic acid) of the carrier peptide to produce a new araide linkage between the amine of the iodothyronine and the acid side chain of the carrier peptide. The amine of the active agent can be covalently attached to the N-terminus or alcohol or amine containing side chains (e.g., serine or lysine) of the carrier peptide with a carbonyl insertion or its equivalent to produce a carbamate or ureide linkage between the iodothyronine's amine group and the carrier peptide. The carboxylic acid group and the amine group of the iodothyronine active agent may be covalently attached to the carrier peptide, thereby, interspersing the active agent within the carrier peptide in a peptide-linked manner In a preferred embodiment, the amino acid is glutamic acid and the iodothyronine active agent or adjuvant is released from the glutamic acid as a dimer upon a hydrolysis of the carrier peptide and wherein the active agent or adjuvant is released from the glutamic acid.

In another preferred embodiment, the glutamic acid is replaced by an amino acid selected from the group consisting of aspartic acid, arginine, asparagine, cysteine, lysine, threonine, and serine, and wherein the active agent is attached to the side chain of the amino acid to form an amide, a thioester, an ester, an ether, a carbonate, an anhydride, or a carbamate. In yet another preferred embodiment, the glutamic acid is replaced by a synthetic amino acid with a pendant group comprising an amine, an alcohol, a sulfhydryl, an amide, a urea, or an acid functionality.

The iodothyronine active agent has an acid group and can be covalently attached to the N-terminus or alcohol or amine containing side chains (e.g., serine or lysine) of the carrier peptide to produce an amide or ester linkage between the iodothyronine's acid group and the carrier peptide.

In a preferred embodiment, the carboxylic acid group and the amine group of the iodothyronine active agent participate in covalent attachment to the carrier peptide, thereby, interspersing the active agent within the carrier peptide in a peptide-linked manner. In another preferred embodiment, the carboxylic acid of the iodothyronine active agent is covalently attached to the N-terminus of the carrier peptide to produce an amide, referred to herein as "N-capped". In another preferred embodiment, the amine of the iodothyronine active agent is covalently attached to the C-terminus of the carrier peptide to produce an amide, referred to herein as "C-capped".

The invention provides a method for preparing a composition comprising a carrier peptide and an iodothyronine active agent covalently attached to the carrier peptide. The method comprises different combinations of the following steps:

(a) forming the N-carboxyanhydride (NCA) of one or more of the 20 naturally occurring amino acids, as illustrated below:

Step A

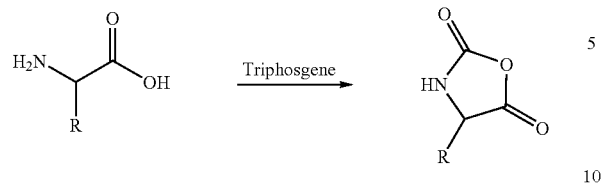

(b) forming the NCA of the iodothyronine active agent, as illustrated below:

Step B

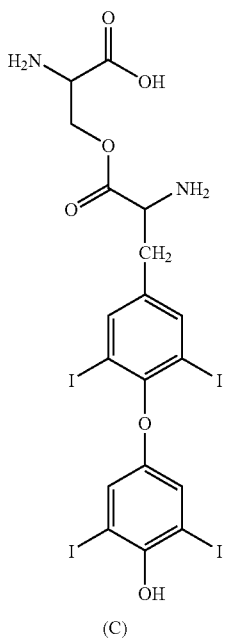

R = Amino acid side chain
HOBt = Hydroxybenzotriazole
DIPC = Diisopropylcarbodiimide
TFA = Trifluoroacetic acid (d) forming an active agent/amino acid complex NCA from the active agent/amino acid complex, as illustrated as follows:

Step D

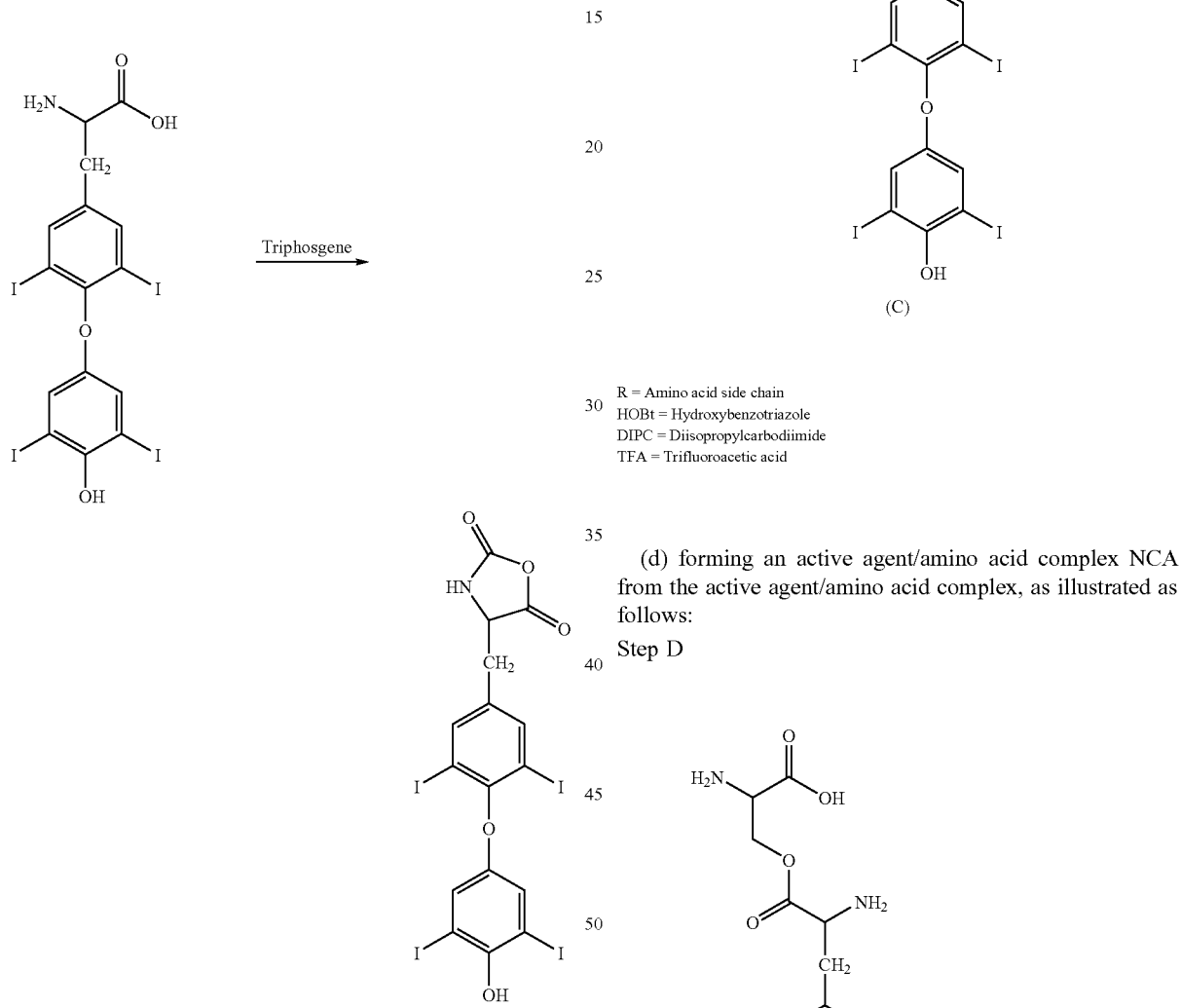

(c) attaching the iodothyronine active agent to a side chain of an amino acid to form an active agent/amino acid complex, as illustrated below:

Step C

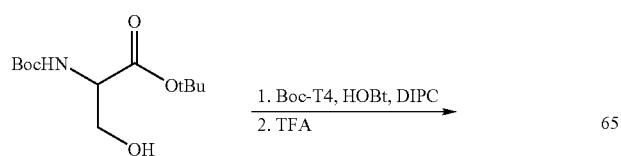

-continued

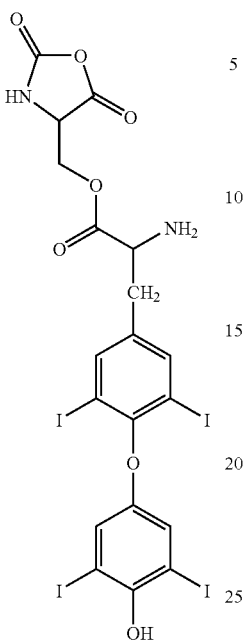

(e) attaching an adjuvant to a side chain of an amino acid to form an adjuvant/amino acid complex, illustrated as follows:
Step E

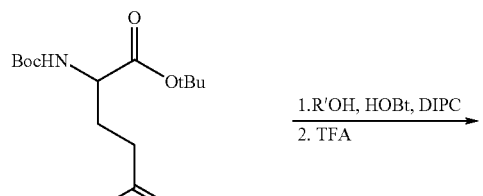

-continued

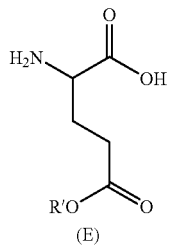

(E)

or (f) forming an adjuvant/amino acid complex NCA from the adjuvant/amino acid complex, illustrated as follows:
Step F

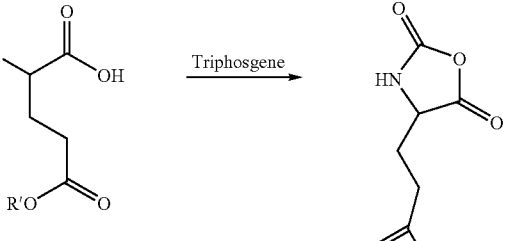

R' = Radical moiety attached to alcohol functionality on drug
HOBt = Hydroxybenzotriazole
DIPC = Diisopropylcarbodiimide
TFA = Trifluoroacetic acid ; and (g) adding an initiator to promote covalent attachment of the key functional groups of the NCA's with concomitant formation of dimers, oligomers or polymers, as shown below:
Step G

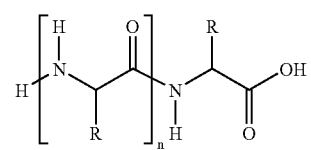

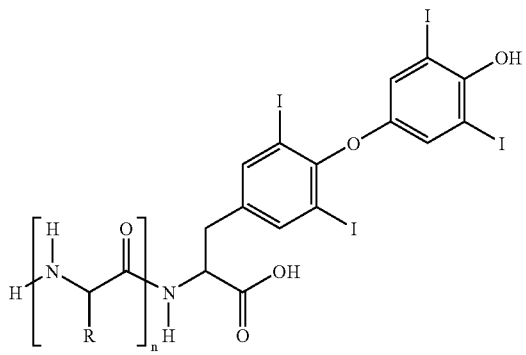

R = Side chain of a peptide, where R can be the side chain of any amino acids, including, but not limited to, T4, T3 and synthetic amino acids with adjuvants attached to the side chain.
R' = Radical moiety attached to alcohol functionality on drug.

The above depiction of how to produce active agent peptide conjugates is meant to be a non-limiting example. One skilled in the art would recognize variations of the above scheme to produce the different embodiments of the present invention.

In one embodiment, the combination of the products of step (a) and (b) or (d) followed by step (g) will produce the iodothyronine active agent-carrier peptide complex of the present invention. In another embodiment of the invention, step (b) will incorporate both thyroid hormones, T4 and T3, in a desired ratio. Combining (a), (b) and (d) followed by step (g) produces an iodothyronine active agent/carrier peptide complex where the iodothyronine active agent is covalently interspersed within the carrier peptide and covalently attached to the side chain of the carrier peptide. Adding (f) to the mixture of (a) and (b) or (d) followed by step (g) produces an iodothyronine active agent/adjuvant/carrier peptide composition.

Figure 3:
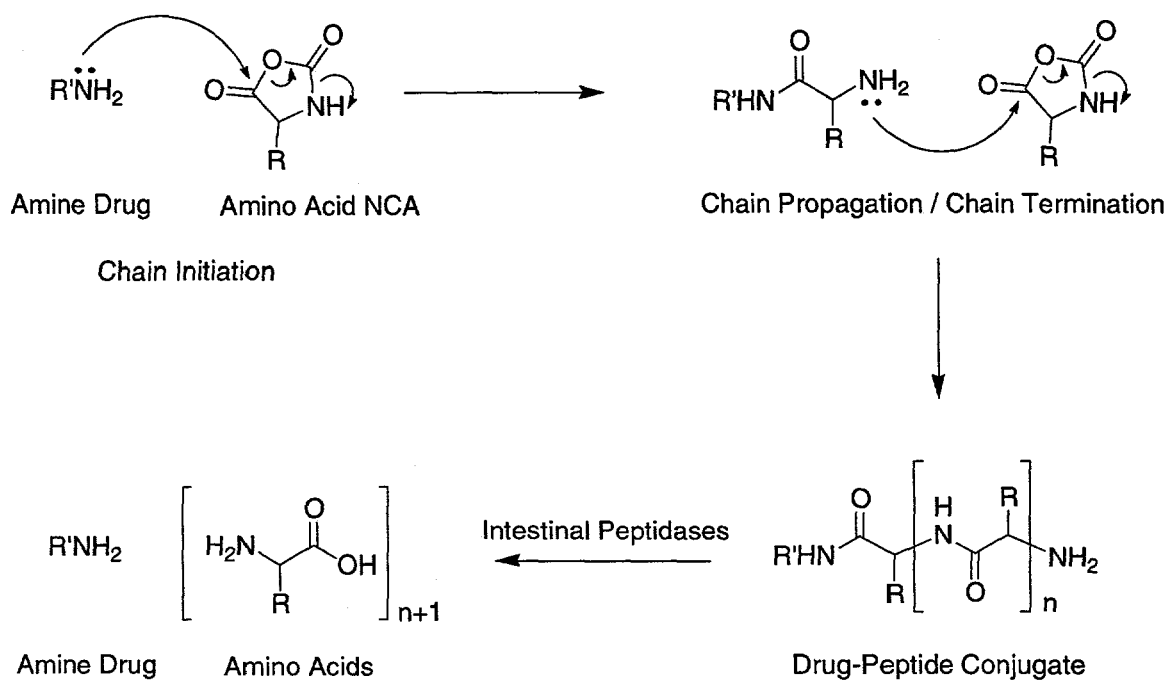
FIG. 3 illustrates the initiation of the activation of an amino acid NCA to initiate the C-terminus attachment of the active agent.
Figure 4:
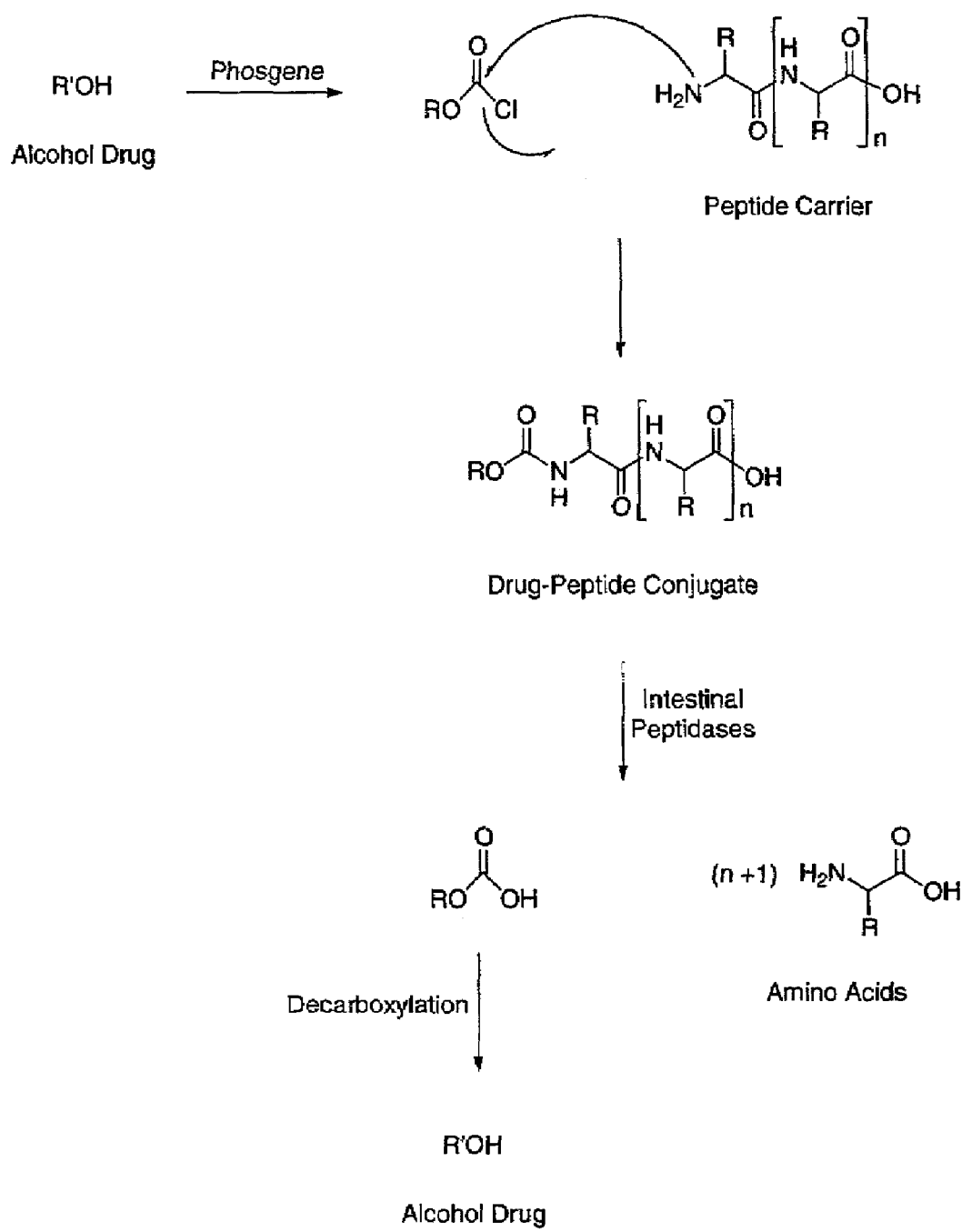
FIG. 4 illustrates the attachment of an alcohol functional group to the N-terminus.
Figure 5:
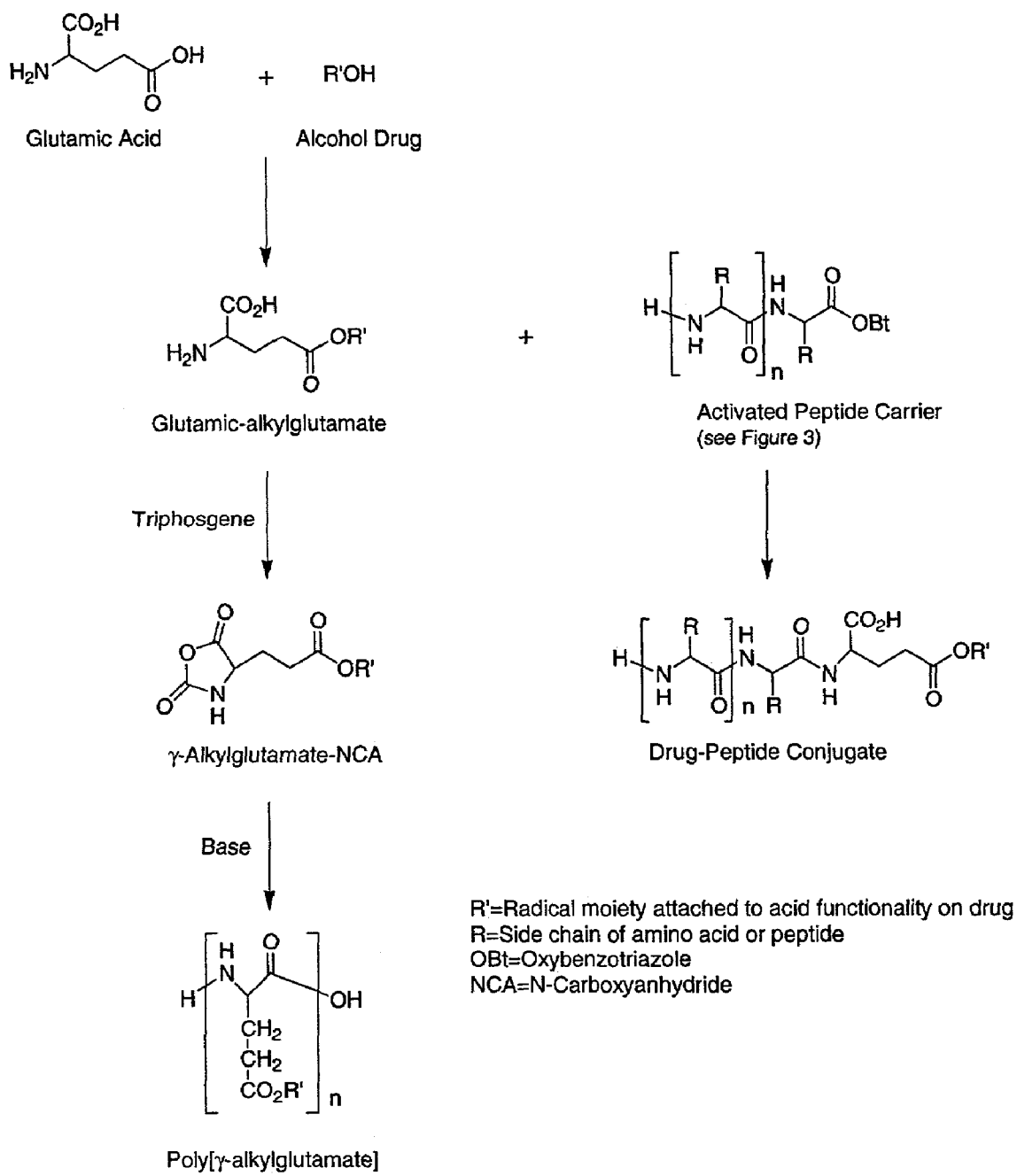
FIG. 5 illustrates an alcohol functional group attached to a glutamic acid dimer.
Figure 6:
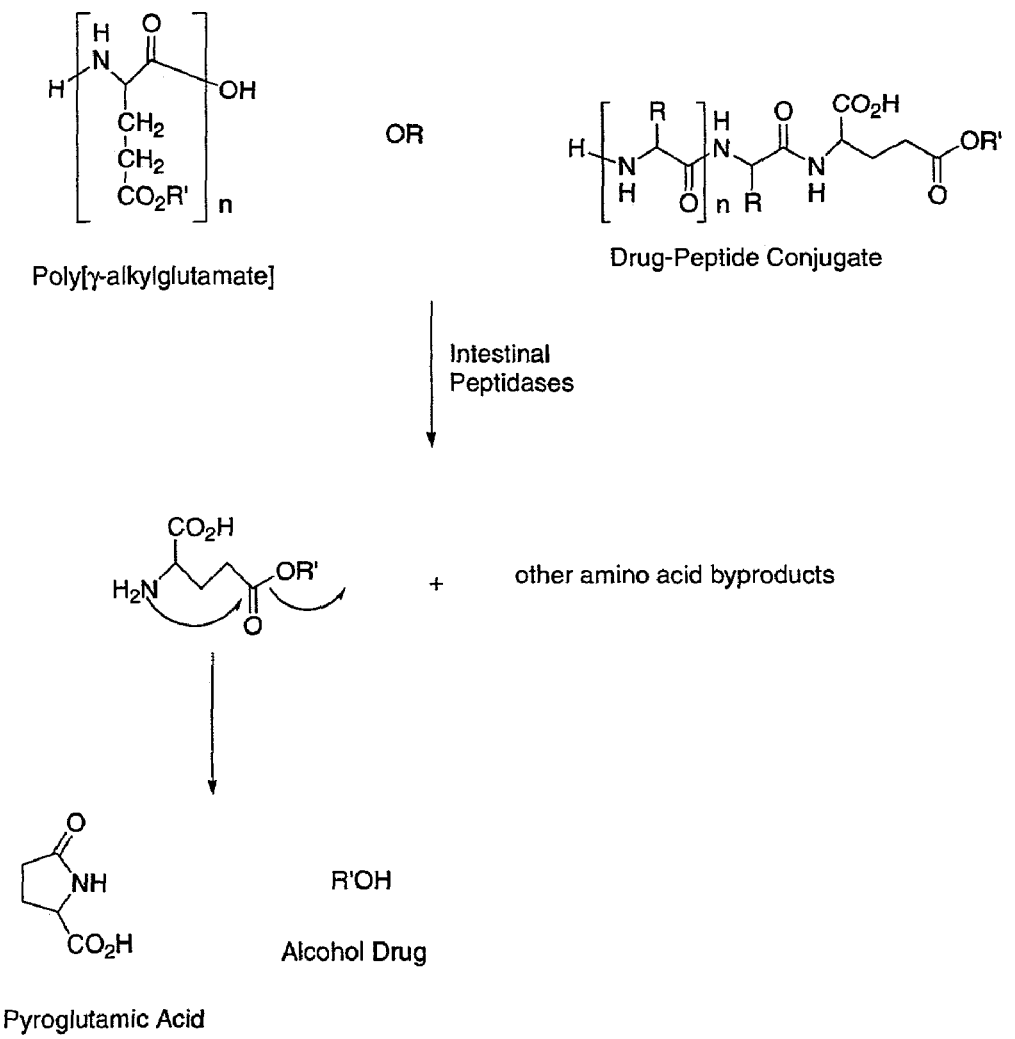
FIG. 6 illustrates a mechanism of release for alcohol group from glutamic acid dimer scheme.

In a preferred embodiment of the invention, step (a) is followed by step (g), wherein the initiator is the iodothyronine active agent, T4 or T3, and wherein said products of these specific steps are C-capped PolyT4 or C-capped PolyT3. (see FIG. 3) In another preferred embodiment of the invention, the sequence of steps, (a) followed by (g), wherein the initiator is a suitably protected amino acid, followed by (b), which may contain T4, T3 or both, followed by deprotection, if necessary, produces N-capped PolyT4, N-capped PolyT3 or N-capped Polythroid. In yet another preferred embodiment, the capped iodothyronine compositions have an iodothyronine:amino acid ratio between 1:4 and 1:1.

Adjuvants can be incorporated into the active agent/carrier peptide composition by following step (f) with step (g), wherein the initiator is the iodothyronine active agent or by following step (b), which may contain T4, T3 or both, with step (g), wherein the initiator is an amino acid from step (e). The products of these sequential steps are capped iodothyronine compositions with an adjuvant attached to every side chain of the carrier peptide. Alternatively, steps (a) and (f) can be combined followed by step (g), wherein the initiator is the iodothyronine active agent, T4 or T3, and wherein said products of these specific steps are C-capped PolyT4 or C-capped PolyT3 with adjuvants on a portion of the side chains of the carrier peptide depending on the (a):(f) ratio.

If a mixture of iodothyronine compounds is desired, the first peptidic iodothyronine composition can be prepared by covalently attaching an iodothyronine active agent to the N-terminus, the C-terminus, and/or a side chain of a carrier peptide; attaching a second iodothyronine compound to the N-terminus, the C-terminus, and/or a side chain of another carrier peptide to form a second peptidic iodothyronine active agent; and then blending the first and second peptidic iodothyronine compositions by known methods.

The carrier peptide can be prepared using conventional techniques. Preferred techniques are reacting mixtures of amino acids and their N-carboxyanhydrides, as described above. Alternatively, if a specific sequence is desired, an automated peptide synthesizer can be used.

The compositions of the invention can also include one or more of a microencapsulating agent, an adjuvant, and a pharmaceutically acceptable excipient. The microencapsulating agent may comprise, for example, lipids, aliphatic alcohols, polypeptides, polyethylene glycol (PEG) or its derivatives, amino acids, carbohydrates, polysaccharides, or salts. In a preferred embodiment, the composition comprises a microencapsulating agent and the active agent-peptide conjugate is released from the composition in a biphasic manner, first, by physicochemical means, such as solvation or swelling of the microencapsulating agent, and then the iodothyronine active agent is released from the carrier peptide by enzymatic action. In another preferred embodiment, a small peptide is covalently attached between the iodothyronine active agent and the microencapsulating agent, wherein release of the active agent from the microencapsulating agent requires both physicochemical and enzymatic action. In certain embodiments (e.g., aliphatic alcohol, carboxylic acids and amidases), the peptide linker is not used and the iodothyronine and alcohol combine to form an ester, which is released in vivo by esterases.

Hydrophilic compounds are absorbed through the intestinal epithelia efficiently via specialized transporters. The entire membrane transport system is intrinsically asymmetric and responds asymmetrically to cofactors. Excitation of the membrane transport system involves a specialized adjuvant resulting in localized delivery of active agents. The invention also allows targeting the mechanisms for intestinal epithelial transport systems to facilitate absorption of active agents.

There are seven known intestinal transport systems classified according to the physical properties of the transported substrate. They include the amino acid, oligopeptide, glucose, monocarboxic acid, phosphate, bile acid, and the P-glycoprotein transport systems and each has its own associated mechanism of transport. The mechanisms can depend on hydrogen ions, sodium ions, binding sites, or other cofactors. Suitable adjuvants, for example, include: papain, which is a potent enzyme for releasing the catalytic domain of aminopeptidase-N into the lumen; glycorecognizers, which activate enzymes in the brush border membrane; and bile acids, which have been attached to peptides to enhance absorption of the peptides.

When an adjuvant is included in the composition, the adjuvant activates an intestinal transporter, bioadheres to the intestinal mucosa, bioadheres to a cell surface under the intestinal mucosa, or a combination thereof. In a preferred embodiment of the invention, one or more of the amino acids of the carrier peptide will activate the intestinal transporter, thereby, increasing the absorption of the iodothyronine active agent. In another preferred embodiment, the composition further comprises an adjuvant covalently attached to the carrier peptide and the enzymatic digestion of the carrier peptide controls release of the adjuvant from the composition. The adjuvant can be microencapsulated into a peptide-drug conjugate for biphasic release of active ingredients, wherein the adjuvant can be released, exclusively, through salvation or swelling of the peptide-drug conjugate.

The attachment of fatty acids to polypeptides can result in improved oral delivery (stability and absorption) in vitro and in vivo (Bundgaard, H.; Hansen, A. *Pharm. International* 1981, June, 136). Reported polypeptides include thyrotropin-releasing hormone (Tanaka, K.; Fujita, T.; Yamamoto, Y.: Murakami, M.; Yamamoto, A.; Muranishi, S. *Biochem. Biophys. Acta*, 1996 1283, 119), insulin (Hashizume, M.; Douen, T.; Murakamai, M.; Yamaoto, A.; Takada, K.; Muranishi, S. *J. Pharm. Pharmacol.*, 1992, 44, 555—Asada, H.; Douen, T.; Waki, M.; Adachi, S.; Fujita, T.; Yamamoto, A.; Muranishi, S. *J. Pharm. Sci.*, 1995, 85, 682), and tetragastrin (Fujita, T.; Kawahara, I.; Quan, Y.; Hattori, K.; Takenaka, K.; Muranishi, S.; Yamamoto, A. *Pharm. Res.*, 1998, 15, 387). The attachment is usually through the N-terminus with the fatty acid having between 2 and 22 carbons with and without unsaturation. In these cases, increased lipophilicity resulted in increased passive uptake and decreased degradation. Thus in another preferred embodiment, the iodothyronine active agent can be covalently attached to a fatty acid, wherein the fatty acid can be a lipid microencapsulating agent or an adjuvant to improve passive absorption.

The attachment of polymers of polyethyleneglycol (PEG) to polypeptides can result in improved oral delivery (solubility and stability) in vivo. Different polypeptides have been PEGylated. PEGylation of these isolated polypeptides often leads to a polydisperse mixture of PEG-peptide conjugates with differing stability, solubility and efficacy. A homogeneous PEG-peptide conjugate would lead to more reproducible pharmacokinetics. A homogeneous population is chemically simpler to prepare with mono-, di-, tri- and short oligiopeptides. The present application shows that T3 attached to the N-terminus of short polyglutamic acid polymers exhibit greater absorption relative to the parent drug alone. In order to protect the more actively absorbed form from premature degradation, attachment of a PEG via a readily chemically or enzymatically labile bond (i.e. ester as opposed to amide) would allow for improved pharmacodynamics. Thus making PEG derivatives of T3 and T4 conjugated to short oligopeptides or even single amino acids would simplify the preparation of T3 and T4 compounds with enhanced stability and absorptive properties. Furthermore, it has been reported that PEG is mucoadhesive and thus conjugated drugs can have increased GI residence time and, putatively, greater absorption (Efremova, N.; Huang, Y.; Peppas, N.; Leckband, D. *Langmuir* 2002, 18, 836–45). PEG mucoadhesion is pH dependent with acidic conditions translating into greater adhesion—even pH 7.2 reportedly allows PEG to adhere to surface bound mucin in the presence of soluble mucin. In another embodiment of the invention, the iodothyronine active agent is covalently attached to PEG, thereby increasing the stability, solubility and intestinal residence time of the iodothyronine active agent.

Cyclodextrins are relatively unique amongst natural products and can serve as chemical hosts. Guest molecules are shielded (stabilized) from the external environment (degradative enzymes) and can be made more hydrophilic or lipophilic depending on the host thus affecting passive and active bioabsorption (Hirayama, F.; Uekama, K. Adv. Drug Deliv. Rev. 1999, 36, 125–141). For example, the immunosuppressive polypeptide Cyclosporin A, a poorly water soluble drug, showed enhanced oral absorption in rats, when co-administered with β-cyclodextrin (Miyake, K.; Arima, J.; Irie, T.; Hirayama, F.; Uekama, K. Biol. Pharm. Bull. 1999, 22(1), 66–72). Cyclodextrins also have low levels of intrinsic toxicity (Irie, T.; Uekama, K. Adv. Drug Deliv. Rev. 1999, 36, 101–123). The association of cyclodextrins with polypeptides can reduce peptide aggregation and deactivation (Brange, J. Stability of Insulin, Kluwer Academic, Boston, 1994). Hydroxy-β-cyclodextrins have been used to deliver thyroid hormones (T3 and T4) to cell cultures of rat hepatocytes and bile duct epithelial cells (2001 Biochem. Pharmacol. May 1;61(9):1073–8). Cyclodextrins have been tested in rats (in situ perfusion) to see the changes in absorption of sulfanilic acid, a non-absorbable drug (1990 Chem Pharm Bull (Tokyo) Jun;38(6):1684–7). Since cyclodextrins are not absorbed except in the colon (broken down by intestinal fauna) they can be used as a delayed colon release drug carrier (2001 J. Pharm. Sci. 90(4), 493 and references within). In yet another embodiment of the invention, the iodothyronine active agent is covalently attached to cyclodextrin to impart protection, improve absorption and target delivery of the iodothyronine active agent.

Preferably, the resultant peptide-active agent conjugate is formulated into a tablet using suitable excipients and can either be wet granulated or dry compressed.

In another embodiment tetraiodothyronine may be made with peptides of D, E, F, G, I, K, L, M, S, T, and V.

Compositions of the invention may comprise the formation of amides from acids and amines and can be prepared by the following examples. Throughout the application the figures are meant to describe the general scheme of attaching active agents through different functional groups to a variety of peptide conjugates resulting in different embodiments of the present invention. One skilled in the art would recognize other reagents, conditions, and properties necessary to conjugate other active agents to other polypeptides from the schemes which are meant to be non-limiting examples. The figures further represent the different embodiments of the present invention with regard to length of the active agent conjugate wherein the amino acid, dipeptide, tripeptide, oligopeptide and polypeptide active agent conjugates can be represented by n=0 for an amino acid, and n≧1 for other peptide embodiments.

EXAMPLES

All reagents were used as received. $^1$H NMR was run on a Bruker 300 MHz (300) or JEOL 500 MHz (500) NMR spectrophotometer using tetramethylsilane as an internal standard. Thin layer chromatography was performed using plates precoated with silica gel 60 $F_{254}$. Flash chromatography was performed using silica gel 60 (230–400 mesh).

The following experimental descriptions provide examples of methods for preparing the various peptidic iodothyronine compositions and intermediates.

I: Preparation of Iodothyronine Conjugates

I:A—Preparation of Glu-NCA

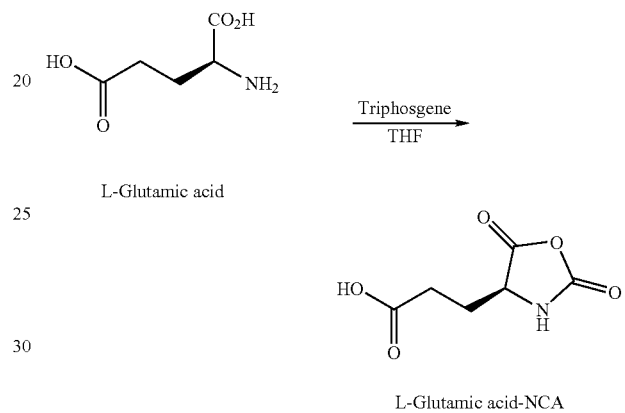

Glu-NCA was prepared by a modification of the protocol reported by Kawai et al., Makromol. Chem., 182, pp. 2127–2137, 1981.

I:B—Preparation of T4-NCA

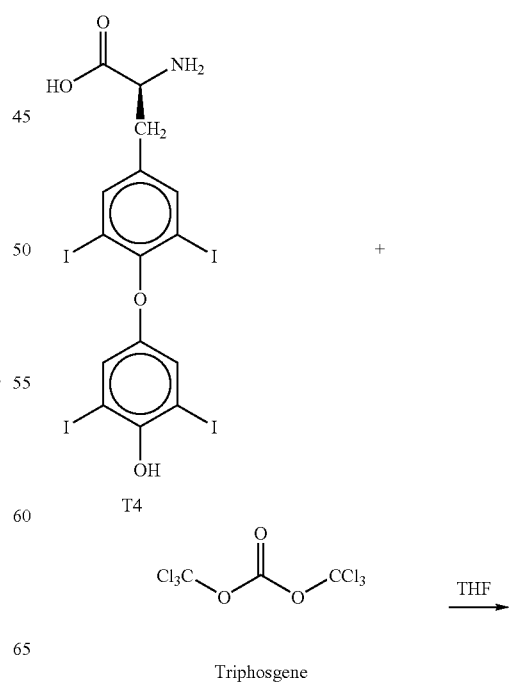

-continued

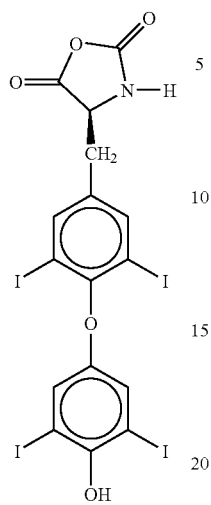

T4-NCA

In a walk-in-fume hood, tetrahydrofuran, THF (255 mL) and L-thyroxine, T4 (776.9 g.mol$^{-1}$, 65.6 mmol, 51.0 g) were charged into a 3-neck 500 mL round bottom flask fit with a heating mantle and a magnetic stirrer. The mixture was stirred under nitrogen at room temperature until T4 is dissolved. After the addition of triphosgene (296.75 g.mol$^{-1}$, 45.4 mmol, 13.5 g), the reaction mixture was gradually heated to 60° C. over 15 minutes and maintained at this temperature throughout the course of the reaction. An additional 12.8 g of triphosgene was added after 5 hours and the reaction was heated for 3 additional hours. The reaction was cooled down to room temperature, and the solution was added to 3 L of n-heptane with stirring. The solid was collected by filtration and washed with 2 portions of 200 mL of n-heptane. The solid was dried under vacuum at room temperature. Yield: 45.3 g (86%)

I:C—Preparation of T3-NCA

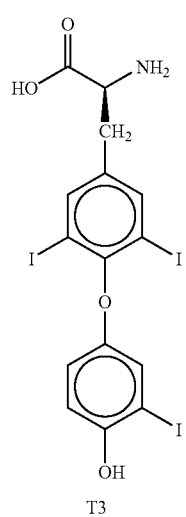

T3

+

-continued

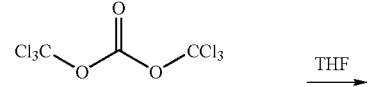

Triphosgene

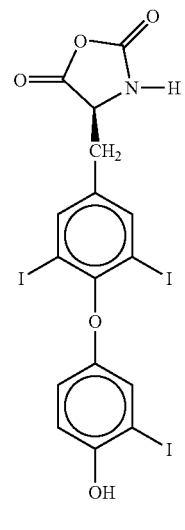

T3-NCA

The reaction was carried out as described above using 3,3',5-triiodo-L-thyronine, T3 (651.0 g.mol$^{-1}$, 78.3 mmol, 51.0 g), triphosgene (296.75 g.mol$^{-1}$, 61.9 mmol, 18.4 g), and THF (281 mL). An additional 2.0 g of triphosgene was added after 4 hours, and the reaction was heated for an additional hour. The reaction mixture was cooled down at room temperature, and the solution was slowly added to 2040 mL of n-heptane with stirring. The white crystals were collected by filtration and dried under vacuum. Yield: 41.0 g. (77.3%)

I:D—Preparation of the Polymers by Glu-NCA Method
  (i) 25 g Scale Batch of N-Capped PolyT4 (R-I-168)

|  | Glu-NCA | MSG[1] | T4-NCA | DMF |
|---|---|---|---|---|
| Lot# | LO-IV-151 | (NA) | LO-IV-195B[3] |  |
| MW (g · mol$^{-1}$) | 173.0 | 169.1 | 803.0 |  |
| Amt | 25 g | 1.629 g | 6.255 g | 125 mL |
| mmoles | 144.509 | 9.634 | 7.707 |  |
| Eq. | 1 | 1/15 | (1/15) × 0.8[2] |  |

[1]L-glutamic acid, monosodium salt.
[2]considering that 20% of Glu-NCA turns into pyroglutamic acid and that only 80% is available to react with T4-NCA.
[3]98.94% pure.

The reaction was done under argon, in oven-dried glassware. Glu-NCA was dissolved in dry N,N-dimethylformamide, DMF, MSG was then added and stirred for 24 hours at low temperature. T4-NCA was added, and stirred for 24 more hours at room temperature. The reactant mixture was poured into 2.5 L of water, pH was adjusted to 1.93 with 6N hydrochloric acid, HCl and was refrigerated for 1–2 hours. A white solid was filtered and dried under high vacuum. Washed with 2×500 mL of 60° C. ethanol, EtOH and 10×250 mL of 70° C. water. Dried under high vacuum. (Yield: 16.208 g)

(ii) 25 g Scale Batch of N-Capped PolyT3 (R-I-169)

|  | Glu-NCA | MSG[1] | T3-NCA | DMF |
|---|---|---|---|---|
| Lot# | LO-IV-171 | (NA) | LO-IV-195A[4] |  |
| MW (g · mol$^{-1}$) | 173.0 | 169.1 | 677.0 |  |
| Amt | 25 g | 1.629 g | 5.516 g | 125 mL |
| mmoles | 144.509 | 9.634 | 7.707 |  |
| Eq. | 1 | 1/15 | (1/15) × 0.8[2] |  |

[1] L-glutamic acid, monosodium salt.
[2] considering that 20% of Glu-NCA turns into pyroglutamic acid and that only 80% is available to react with T4-NCA.
[4] 94.95% pure.

The reaction was done under argon, in oven-dried glassware. Glu-NCA was dissolved in dry DMF, MSG was added and stirred for 24 hours at low temperature. T3-NCA was added, and stirred for 24 more hours at room temperature. Reactant mixture was poured into 2.5 L of water, pH was adjusted to 1.93 with 6N HCl and refrigerated for 1–2 hours. A white solid was filtered, dried under high vacuum. Washed with 2×500 mL of 60° C. EtOH and 10×250 mL of 70° C. water. Dried under high vacuum. (Yield: 17.282 g)

(iii) 1 g-Scale Batch of C-Capped Polythroid (LO-IV-182)

|  | Glu-NCA | T4[5] | T3[6] | DMF |
|---|---|---|---|---|
| Lot# | LO-IV-127B | 40K12671 | 100K1517 |  |
| MW (g · mol$^{-1}$) | 173.0 | 776.9 | 651.0 |  |
| Amt | 1 g | 264.16 mg | 29.5 mg | 10 mL |
| mmoles | 5.78 | 0.34 | 0.05 |  |
| Eq. | 1 | 1/17 | 1/127.5 |  |

[5] T4, L-Thyroxine, Sigma T2376
[6] T3, 3,3',5-triiodo-L-thyronine, Sigma T2877

The reaction was done under argon, in oven-dried glassware. Glu-NCA was dissolved in dry DMF and stirred for 5–10 minutes at room temperature. T3 and T4 were added, and stirred overnight at room temperature. The reactant mixture was poured into 100 mL of water, pH was adjusted to 1.60 with 6N HCl and refrigerated for 1–2 hours. A white solid was filtered and dried under high vacuum. Solid was sitrred in 100 mL of 70° C. water for 15–20 minutes. Solid was filtered. Stirred in 100 mL of 60° C. EtOH for 15 minutes. Solid was filtered and dried under high vacuum at 60° C. (Yield: 673.9 mg)

(iv) Preparation of Random Polythroid

Glutamic acid-NCA
+
T4-NCA
+
T3-NCA
+
Triethylamine

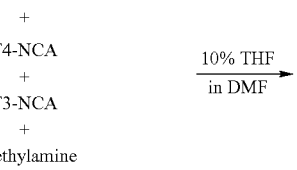

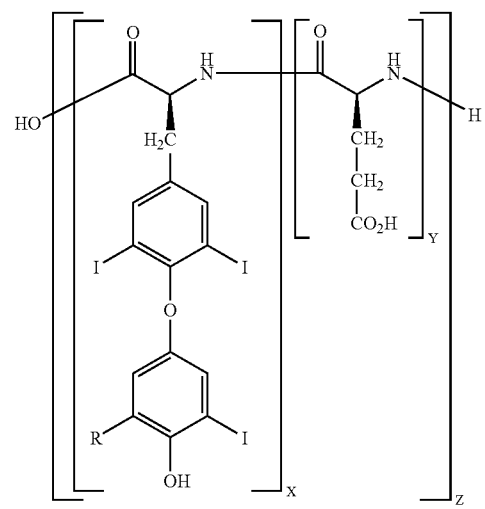

R = H, T3; R = I, T4

In a round bottom flask fit with a nitrogen bubbler and a magnetic stirrer, Glu-NCA (173 g.mol$^{-1}$, 0.69 mol, 119.9 g), T4-NCA (802 g.mol$^{-1}$, 47.0 mmol, 37.7 g), and T3-NCA (677 g.mol$^{-1}$, 6.27 mmol, 4.2 g) were dissolved in a mixture of DMF (275 mL) and THF (30 mL). After the addition of triethylamine (101 g.mol$^{-1}$, 46.4 mmol, 4.7 g), the reaction was stirred at room temperature for 18 hours. The viscous amber solution was added drop wise to 5 L of distilled water. During the addition, the suspension was stirred vigorously for 1 hour using a mechanical stirrer. The slurry was filtered using a Buchner funnel with Whatman #4 paper, and the off-white cake was washed with 530 mL of distilled water. The solid was re-suspended in 2 L of distilled water and heated to 70° C. Held at 70° C. for 15 minutes. Cooled to 5° C. Filtered off to collect off-white precipitate, which was washed with 180 mL of distilled water. Dried in vacuo (28 in Hg) at 70–75° C. overnight. Yield: 72 g In a preferred embodiment the amount of Glutamic acid-NCA used is 110.5 eq; T4-NCA is 7.5 eq; T3-NCA is 1 eq. and triethylamine is 7.4 eq. In another preferred embodiment Z=1, R=H (T3) or R=I (T4), X=1 and Y=8–10. In another preferred embodiment Z=1, R=H (T3) or R=I (T4), X=1 and Y=1–3.

(v) Preparation of Random PolyT4

Glutamic acid-NCA
+
T4-NCA
+
Triethylamine

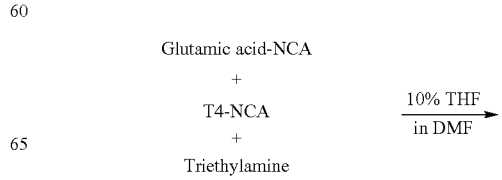

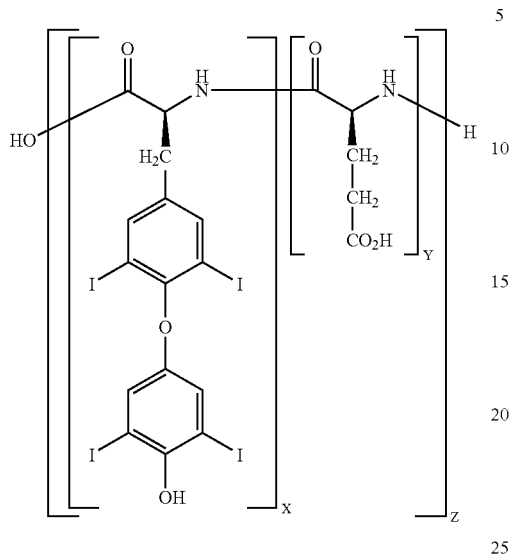

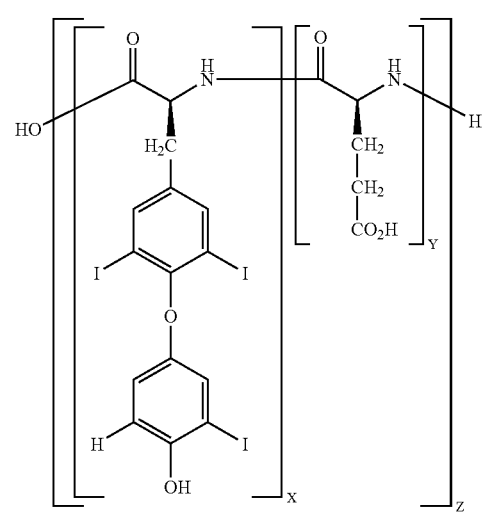

In a round bottom flask fit with a nitrogen bubbler and a magnetic stirrer, Glu-NCA (173 g.mol$^{-1}$, 3.18 mol, 550 g) and T4-NCA (802 g.mol$^{-1}$, 0.24 mol, 196.3 g) were dissolved in a mixture of DMF (1536 mL) and THF (154 mL). After the addition of triethylamine (101 g.mol$^{-1}$, 0.24 mol, 34.1 mL), the reaction was stirred at room temperature for 15 hours. The viscous amber solution was added drop wise to 29 L of sterile water. During the addition, the suspension was stirred vigorously for 1 hour using a mechanical stirrer. The slurry was filtered through a filter funnel using a polypropylene filter pad. The off-white cake was washed with 3×1 L of sterile water, re-suspended in 9 L of sterile water, heated to 40° C. and held at this temperature for approximately 2 hours, cooled to room temperature. Filtered off to collect off-white precipitate. The washing procedure was repeated twice. Dried in vacuo (28 in Hg) at 70–75° C. overnight. Yield: 430 g In a preferred embodiment the amount of Glutamic acid-NCA used is 13.25 eq; T4-NCA is 1 eq; and triethylamine is 1 eq. In another preferred embodiment Z=1, X=1 and Y=8–10. In another preferred embodiment Z=1, X=1 and Y=1–3.

(vi) Preparation of Random PolyT3

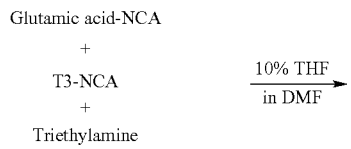

In a round bottom flask fit with a nitrogen bubbler and a magnetic stirrer, Glu-NCA (173 g.mol$^{-1}$, 1.924 mol, 332.9 g) and T3-NCA (677 g.mol$^{-1}$, 0.148 mol, 100 g) were dissolved in a mixture of DMF (915 mL) and THF (91.5 mL). After the addition of triethylamine (101 g.mol$^{-1}$, 0.137 mol, 19.1 mL), the reaction was stirred at room temperature for 18 hours. The viscous amber solution was added drop wise to 17.6 L of sterile water. During the addition, the suspension was stirred vigorously for 1 hour using a mechanical stirrer. The slurry was filtered through a filter funnel using a polypropylene filter pad. The off-white cake was washed with 3×1 L of sterile water, re-suspended in 8 L of sterile water, heated to 40° C. and held at this temperature for approximately 2 hours, cooled to room temperature. Filtered off to collect off-white precipitate. The washing procedure was repeated twice. Dried in vacuo (28 in Hg) at 70–75° C. overnight. Yield: 221 g In a preferred embodiment the amount of Glutamic acid-NCA used is 14.04 eq; T3-NCA is 1.08 eq; and triethylamine is 1 eq. In another preferred embodiment Z=1, X=1 and Y=8–10. In another preferred embodiment Z=1, X=1 and Y=1–3.

II: Synthesis of Poly-T3 on Resin

1. Suitable amounts Fmoc-T3 were prepared for each synthesis.
2. Suitable amounts of Fmoc-Glu(OtBu)-OH were prepared for each synthesis.
3. Suitable amounts of Fmoc-Glu(OtBu)4-OH were prepared for each synthesis.
4. Compound H-(T3)EE-OH was prepared by direct step wise synthesis of Fmoc-Glu(OtBu)-OH (two times) and then Fmoc-T3. Then it was cleaved, deprotected, purified and characterized according to the standard protocols methods known by one skilled in the art.

5. Compound H-EEE(T3)EE-OH (SEQ ID NO: 1) was prepared by direct step wise synthesis of Fmoc-Glu (OtBu)-OH and Fmoc-T3. Then it was cleaved, deprotected, purified and characterized.
6. Compound H-EEEEEE(T3)EEE-OH (SEQ ID NO: 2) was prepared by direct step wise synthesis from the C-terminus up to H-EE(T3)EEE-O-resin (SEQ ID NO: 3), then Fmoc-Glu(OtBu)4 was condensed with this intermediate. Then it was cleaved, deprotected, purified and characterized.
7. Compound H-EEEEEEEEEEEEEEE(T3)EEEE-OH (SEQ ID NO: 4) was prepared by direct step wise synthesis from the C-terminus up to H-EEE(T3)EEEE-O-resin (SEQ ID NO: 5). Successive blocks of Fmoc-Glu (OtBu)4-OH were condensed with the resin, the peptide was cleaved, purified and characterized according to the standard protocols methods know by one skilled in the art.

The above protocol provides a description of how to make preferred embodiments of the present invention including T3-Glu-Glu and random T3-Glu, wherein there is one T3 to every eight to 10 Glu. One skilled in the art would appreciate other variations and embodiments thereof.

III: Description of Various other Methods for Making Iodothyronine Compositions

III:A

The following experiment descriptions provide examples of alternative methods of preparing various peptidic iodothyronine compositions.

(i) Preparation of Teoc-T3

To a stirred suspension of T3 (651 g.mol$^{-1}$, 1.30 g, 2.0 mmoles) in Methyl Sulfoxide, DMSO (10 mL) was added triethylamine (101.2 g.mol$^{-1}$, 0.726 g.cm$^{-3}$, 418 µL, 3.0 mmoles) followed by solid 1-[2-(trimethylsilyl)ethoxycarbonyloxy]pyrrolidin-2,5-dione, Teoc-OSu (259.3 g.mol$^{-1}$, 571 mg, 2.2 mmoles). The mixture was stirred overnight at room temperature, then diluted with water (30 mL), acidified with saturated potassium hydrogen solution to pH=2–3, and extracted with ethyl acetate, EtOAc (3×50 mL). The combined organic layers were washed with water (1×50 mL), dried with magnesium sulfate, filtered, and evaporated. Yield: 1.76 g.

Teoc-OSu was prepared according to the protocol reported by Shute et al (April 1987, Synthesis, 346–348).

(ii) Preparation of Teoc-T4

To a stirred suspension of T4 (777 g.mol$^{-1}$, 7.53 g, 9.7 mmoles) in Methyl Sulfoxide, DMSO (50 mL) was added triethylamine (101.2 g.mol$^{-1}$, 0.726 g.cm$^{31\ 3}$, 2.03 mL, 14.5 mmoles) followed by solid Teoc-OSu (259.3 g.mol$^{-1}$, 2.76 g, 10.7 mmoles). The mixture was stirred overnight at room temperature, then diluted with water to 100 mL, acidified with saturated potassium hydrogen solution to pH=2–3, and extracted with ether (3×100 mL) and EtOAc (1×50 mL). The combined organic layers were washed with water (2×100 mL), dried with magnesium sulfate, filtered, and evaporated. Yield: 8.40 g.

Teoc-OSu was prepared according to the protocol reported by Shute et al (April 1987, Synthesis, 346–348).

(iii) Iodothyronine Conjugation to Peptide N-terminus

N-protected T4, N-protected T3 or both is dissolved in DMF under nitrogen and cooled to 0° C. The solution is treated with diisopropylcarbodiimide and hydroxybenzotriazole followed by the peptide carrier. The reaction is stirred for several hours at room temperature, the urea by-product filtered off, and the product precipitated out in ether, and purified using gel permeation chromatography (GPC) or dialysis.

The N-protecting group is selected from any of the amine protecting groups known by one skilled in the art. In a preferred embodiment the protecting group is the 9-Fluorenylmethyloxycarbonyl (Fmoc) group. In a most preferred embodiment the protecting group is the 2-(trimethylsilyl) ethoxycarbonyl (Teoc) group.

(iv) Iodothyronine Conjugation to Peptide C-terminus

The peptide carrier is dissolved in DMF under nitrogen and cooled to 0° C. The solution is treated with diisopropylcarbodiirde and hydroxybenzotriazole followed by the T4, T3 or both. The reaction is stirred for several hours at room temperature, the urea by-product filtered off, and the product precipitated out in ether, and purified using GPC or dialysis.

(v) Iodothyronine Alcohol Conjugation to Peptide N-Terminus

In the following example, the alcohol of N-protected T4 or N-protected T3 is allowed to react with triphosgene in dry DMF producing a chloroformate, which when reacted with the N-terminus of the peptide produces a carbamate. The suitably protected peptide carrier is then added slowly and the solution stirred at room temperature for several hours. The product is then precipitated out in ether. The crude product is suitably deprotected and purified using GPC. Deprotection by the usual method yields the desired Peptidic N-terminus Iodothyronine Carbamate.

The N-protecting group is selected from any of the amine protecting groups known by one skilled in the art. In a preferred embodiment the protecting group is the 9-Fluorenylmethyloxycarbonyl (Fmoc) group. In a most preferred embodiment the protecting group is the 2-(trimethylsilyl) ethoxycarbonyl (Teoc) group.

III:B

The following experimental descriptions provide examples of methods of preparing the various side-chain attached peptidic compositions. The alkyl groups can be an adjuvant or an iodothyronine active agent.

(i) Active Agent Conjugation to γ-Alkyl Glutamate and C-Terminus

The dimer, oligomer or polymer of glutamic acid is dissolved in DMF under nitrogen and cooled to 0° C. The solution is treated with diisopropylcarbodiimide and hydroxybenzotriazole followed by the alcohol (e.g., T4, T3 or adjuvant). The reaction is stirred for several hours at room temperature, the urea by-product filtered off, and the product precipitated out in ether, and purified using GPC or dialysis.

(ii) Preparation of γ-Alkyl Glutamate

A suspension of glutamic acid, the alcohol and concentrated hydrochloric acid are mixed and heated with stirring for several hours. The γ-alkyl glutamate product is precipitated out in acetone, filtered, dried and recrystallized from hot water.

(iii) Preparation of γ-Alkyl Glutamate-NCA

γ-Alkyl glutamate is suspended in dry THF where triphosgene is added and the mixture refluxed under a nitrogen atmosphere until the mixture becomes homogenous. The solution is poured into heptane to precipitate the NCA product, which is filtered, dried, and recrystallized from a suitable solvent.

(iv) Preparation of Poly[γ-Alkyl Glutamate]

γ-Alkyl glutamate-NCA is dissolved in dry DMF where a catalytic amount of a primary amine can be added to the solution until it becomes viscous (typically overnight). The product is isolated from the solution by pouring it into water and filtering. The product can be purified using GPC or dialysis.

III:C

The following experimental conditions describe the attachment of the lipophilic adjuvant, the benzyl group, to the side chain of glutamic acid and the subsequent polymerization.

(i) Preparation of Benzylglutamic Acid-NCA

Benzylglutamic acid (25 grams) was suspended in 400 mL of anhydrous EtOAc, under nitrogen. The mixture was heated to reflux where 30 grams of triphosgene was added in six equal portions. The reaction was refluxed for three hours until homogenous. The solution was cooled to room temperature, filtered, and concentrated in vacuo. The white powder was recrystallized from 50 mL of hot anhydrous EtOAc to yield 17.4 grams (63%) of a white powder.

(ii) Preparation of Polybenzylglutamic Acid

Benzylglutamic acid (17.4 grams) was dissolved in anhydrous THF under nitrogen where 238 mg of sodium methoxide was added portionwise. The solution was stirred for two days with a marked increase in viscosity. The solution was poured into 1.5 L of petroleum ether with stirring. The petroleum ether was decanted off and an additional 1 L of petroleum ether was added back. The mixture was stirred by hand, the petroleum ether was decanted off and the process repeated with 500 mL of petroleum ether. The white solid was air-dried and then vacuum dried to yield 14.7 (95%) of a white fluffy paper-like solid.

(iii) Preparation of Polyglutamic Acid

Acetic acid (10 mL) was stirred with 10 mL of 30 wt % hydrogen bromide, HBr in acetic acid where 1.96 g of polybenzylglutamic acid was added portionwise. The mixture was stirred at room temperature for one day and was, then, added to 50 mL of ether. The white precipitant was filtered, washed with 4×30 mL of ether and dried under a high vacuum to yield 1.11 grams (97%) of a white powder.

Other solvents, activating agents, co-catalysts and bases can be used. Examples of other solvents include dimethylsulfoxide, ethers such as tetrahydrofuran or chlorinated solvents such as chloroform. Examples of other activating agents include 1,3-dicyclohexylcarbodiimide, DCC, diisopropylcarbodiimide or thionyl chloride. An example of another co-catalyst is N-hydroxysuccinimide. Examples of bases include pyrrolidinopyridine, dimethylaminopyridine, triethylamine, or tributylamine.

IV: Fatty Acid Acylation (i) Preparation of N-Palmitoyl-L-triiodothyronine (C16T3)

To palmitic acid (0.500 g, 2.0 mmol) in 5 mL of dichloromethane, $C_2Cl_2$, was added DCC (0.201 g, 1.0 mmol). The solution was allowed to stir for 45 minutes whereupon it was filtered through glasswool to remove insoluble 1,3-dicyclohexylurea, DCU, into 3 mL of DMF containing L-triiodothyronine (0.578 g, 0.9 mmol) and N-dimethyl-4-aminopyridine (0.119 g, 1.0 mmol). After stirring for 18 h the solvent was removed by rotary evaporation and the residue purified by flash chromatography (30:1–8:1 $CHCl_3:CH_3OH$ with 1 drop HOAc/100 mL eluent) to provide the target as a white solid (0.242 g, 31%): $R_f$ (6:1 $CHCl_3:CH_3OH$) 0.27; $^1H$ NMR ($CDCl_3$ 500 MHz) 8.10 (d, 2H), 7.63 (s, 1H, NH), 7.06–6.48 (m, 3H), 4.64 (bs, 1H, α), 3.12 (m, 2H, β), 2.16 (m, 2H), 1.55 (m, 2H), 1.33–1.10 (bs, 24H), 0.83 (t, 3H).

(ii) Prepartion of N-Octanoyl-L-triiodothyronine(O-octanoyl) (C8T3(C8))

To octanoic acid (0.30 mL, 1.9 mmol) in 5 mL of $CH_2Cl_2$ was added DCC (0.201 g, 1.0 mmol). The solution was allowed to stir for 30 minutes whereupon it was filtered through glasswool to remove insoluble DCU into 3 mL of DMF containing L-triiodothyronine (0.578 g, 0.9 mmol) and N-dimethyl-4-aminopyridine (0.217 g, 1.8 mmol). After stirring for 16 h the solvent was removed by rotary evaporation and the residue purified by flash chromatography (30:1–8:1 $CHCl_3:CH_3OH$ with 1 drop HOAc/100 mL eluent) to provide the target as a white solid (0.473 g, 64%): $R_f$ (6:1 $CHCl_3:CH_3OH$) 0.16; $^1H$ NMR ($CDCl_3$ 500 MHz) 8.16 (d, 2H), 7.65 (s, 1H, NH), 7.11–6.52 (m, 3H), 4.68 (dd, 1H, α), 3.17 (dd, 1H, β), 3.08 (dd, 1H, β), 2.28 (m, 4H), 1.61 (m, 4H), 1.29–1.20 (bs, 16H), 0.85 (m, 6H).

(iii) Prepartion of Triiodothyronine Octanoate—TFA (T3C8)

a) To TeocT3 (0.300 g, 0.38 mmol) in 3 mL of dry DMF was added DCC (0.086 g, 0.42 mmol), 1-octanol (0.2 mL, 1.2 mmol) and N-dimethyl-4-aminopyridine (0.051 g, 0.42 mmol). After stirring for 21 h the solvent was removed by rotary evaporation and the residue purified by flash chromatography (12:1–0:1 hexane:EtOAc) to provide the target as a white solid (0.187 g, 55%): $R_f$ (1:1 hexane:EtOAc) 0.95; $^1H$ NMR ($CDCl_3$ 500 MHz) 7.62 (s, 2H), 7.11–6.57 (m, 3H), 5.29 (d, 1H, NH), 4.57 (m, 1H, α), 4.08 (m, 4H, $C(O)OCH_2$alkyl, $CH_2OC(O)N$), 2.88 (m, 2H, β), 2.28 (m, 4H), 1.57 (m, 2H, $OCH_2CH_2$alkyl), 1.30–1.24 (m, 10H), 0.96 (m, 2H, $SiCH_2$), 0.84 (m, 3H, $CH_3$).

b) TeocT3C8 material (0.187 g, 0.21 mmol) was dissolved in 10 mL of $CH_2Cl_2$ and 5 mL of trifluoroacetic acid, TFA. After stirring for 1 h the solvent was removed by rotary evaporation target as a white solid (0.177 g, 100%): $R_f$ (1:1 hexane:EtOAc) 0.78; $^1H$ NMR (DMSO 500 MHz) 7.83 (s, 2H), 6.95–6.66 (m, 3H), 4.45 (m, 1H, α), 4.13 (m, 2H, $C(O)OCH_2$alkyl), 3.30 (m, 1H, β), 3.06 (m, 1H, β), 2.00 (m, 2H), 1.52 (m, 2H), 1.30–1.25 (m, 10), 0.86 (m, 3H, $CH_3$).

(iv) Preparation of Trioodothyronine Hexadeconoate—TFA (T3C16)

a) To TeocT3 (0.300 g, 0.38 mmol) in 3 mL of dry DMF was added DCC (0.086 g, 0.42 mmol), 1-hexadecanol (0.274 g, 1.13 mmol) and N-dimethyl-4-aminopyridine (0.051 g, 0.42 mmol). After stirring for 18.5 h the solvent was removed by rotary evaporation and the residue purified by flash chromatography (12:1–0:1 hexane:EtOAc) to provide the target as a white solid contaminated with 1-hexadecanol (0.348 g, 90%): $R_f$ (3:1 hexane:EtOAc) 0.46; $^1H$ NMR ($CDCl_3$ 500 MHz) 7.63 (s, 2H), 7.08–6.62 (m, 3H), 5.29 (d, 1H, NH), 4.56 (m, 1H, α), 4.11 (m, 4H, $C(O)OCH_2$alkyl, $CH_2OC(O)N$), 2.99 (m, 2H, β), 2.28 (m, 4H), 1.55 (m, 2H, $OCH_2CH_2$alkyl), 1.31–1.24 (m, 26H), 0.96 (m, 2H, $SiCH_2$), 0.86 (m, 3H, $CH_3$).

b) The impure TeocT3C16 material (0.348 g) was dissolved in 10 mL of $CH_2Cl_2$ and 5 mL of TFA. After stirring for 1 h the solvent was removed by rotary evaporation target as a white solid: $R_f$ (1:1 hexane:EtOAc) 0.85; $^1H$ NMR (DMSO 500 MHz) 7.84 (s, 2H), 6.95–6.64 (m, 3H), 4.45 (m, 1H, α), 4.10 (m, 2H, $C(O)OCH_2$alkyl), 3.30 (m, 1H, β), 3.06 (m, 1H, β), 2.00 (m, 2H), 1.52 (m, 2H), 1.30–1.25 (m, 10), 0.86 (m, 3H, $CH_3$).

V: Synthesis of mPEG-Amine-Triiodothyronine (i) Synthesis of mPEG-Teoc-T3

To a stirring solution of Teoc-T3 (88 mg, 0.11 mmol) in 3 mL of dry DMF under Ar was added DCC (25 mg, 1.20 mmol). After stirring overnight the insoluble DCU was filtered and the solid byproduct was washed with 2 mL of DMF. To the combined clear filtrates was added mPEG-amine (534 mg, 0.10 mmol, average MW=5336) and 3 mL additional DMF. The solution was heated briefly with a heat gun until all of the amine was dissolved. The reaction was allowed to stir at room temperature overnight. The reaction solution was poured into 50 mL of diethylether causing the product to crash out as a white solid which was filtered. The solid product was then dissolved into 10 mL of DMF and poured into 50 mL of ether once again. This process was repeated one additional time and the filtered solid was dried by high vacuum overnight yielding 340 mg (56%) of the hygroscopic product.

(ii) Deprotection of mPEG-Teoc-T3

The dried product from part A was stirred in 3 mL of TFA at room temperature for one hour. The TFA was removed by rotary evaporation of the azeotrope with hexane. The residue was dissolved in 3 mL of DMF and this solution was poured into 50 mL of ether. This suspension was cooled to 4° C., filtered and dried by high vacuum for 5 hours. This material was further purified by ultrafiltration (3,000 MW) filter using saturated sodium bicarbonate as a diluent. The product was dissolved in 10 mL of diluent and passed through the filter at 40 psi the rinsed in a similar manner 4 times. The residue was taken up in 3 mL of water and the filter was rinsed two additional times with 3 mL of water. The combined solution was frozen and lyophilized resulting in 162 mg (55%) of a fluffy white powder. T3 quantity present in conjugate by UV potency ($\lambda_{320}$, 1 M NaOH) was determined to 5.3% of total mass.

VI: Preparation of Triiodothyronine Cyclodextrin Ester

To TeocT3 (0.457 g, 0.57 mmol) in 5 mL dry DMF was added DCC (0.237 g, 1.15 mmol). After stirring for 40 min under Ar was added β-cyclodextrin (0.652 g, 0.57 mmol) and N-dimethyl-4-aminopyridine (0.070 g, 0.57 mmol). After stirring the suspension for 26 h under Ar 20 mL H2O was added. The cloudy white solution was filtered through glasswool and washed with 20 mL EtOAc. The water was removed by lyophilization and the off white residue purified by flash chromatography (C18 CH$_3$OH) to provide roughly a 1:1 mixture of TeocT3-β-CD ($R_f$ 7:7:5:4 EtOAc:2-propanol:NH$_4$OH:H$_2$O) 0.64) and unmodified β-CD ($R_f$ 0.28) as an off-white solid (0.098 g).

VII: In Vitro Performance Studies

VII:A—Materials and Methods of the In Vitro Performance Studies for Testing Lipidated, PEGylated, and Cyclodextrin and Peptide Conjugated Iodothyronine Active Agents Esterase (EC 3.1.1.1; from porcine liver), lipase (EC 3.1.1.3; from porcine pancreas), amidase (EC 3.5.1.4; from *Pseudomonas aeruginosa*), protease (EC 3.4.24.31; type XIV, bacterial from *Streptomyces griseus*; also known as pronase), pancreatin (EC 232-468-9; from porcine pancreas), pepsin (EC 3.4.23.1; from porcine stomach mucosa), tris-HCl, methimazole, 3,3',5-triiodo-L-thyronine (T3), thyroxine (T4) were all purchased from Sigma. Buffers used in the digestive assays were prepared as follows: reducing buffer [110 mM sodium chloride, NaCl, 50 mM methimazole, 40 mM tris-HCl, adjust pH to 8.4 with 1N sodium hydroxide, NaOH], Intestinal Simulator (IS) buffer [100 mM monobasic potassium phosphate, adjust pH to 7.5 with 1N NaOH], Gastric Simulator (GS) buffer [69 mM NaCl, adjust pH to 1.2 with HCl], esterase buffer [10 mM borate buffer pH to 8 with NaOH], lipase and amidase buffer [100 mM monobasic potassium phosphate pH to 7.5 with NaOH].

The proteolytic release of T3 (or T4) from polyglutamic acid conjugates was determined in different assays. Peptide conjugates were shaken at 37° C. in the presence of pronase, pancreatin, esterase, lipase, or amidase for 24 hours or pepsin for 4 hours. Stock solutions of each conjugate (0.5–2.0 mg/mL) and enzymes (protease, reducing buffer, 6 mg/mL; pancreatin, IS buffer, 20 mg/mL; pepsin, GS buffer, 6.40 mg/mL; esterase, esterase buffer, 1.02 mg/mL; lipase, lipase buffer, 0.10 mg/mL; amidase, amidase buffer, 0.10 μl/mL) were prepared. For protease, pancreatin, and pepsin digestion, conjugate and enzyme were diluted 2-fold in the assay in a final volume of 2 mL. After the indicated incubation time for each assay, 2 mL of acetonitrile, MeCN, containing 1% of phosphoric acid, H$_3$PO$_4$, was added to each sample to stop digestion, and samples were centrifuged to remove gross particulate matter. Any remaining particulate was filtered with a 0.2 μm nylon syringe filter (Whatman) prior to HPLC analysis.

Enzyme digested conjugates were analyzed for the presence of unconjugated T3 or T4 by reversed phase HPLC (C18, 4.6×250 mm, 5 μm, 300A) using the following conditions: mobile phase—Lotus buffer (4.5 mL of H$_3$PO$_4$, 8.8 mL triethylamine, pH=3.5)/THF/MeCN [68.6/4.5/26.9] or TBA-phosphate buffer (10 mM tetrabutyl ammonium chloride, 10 mM monobasic sodium phosphate, pH=6.0)/MeCN [65/35]; injection volume—20 μl; flow rate—1 mL/min; UV—230 nm. Retention times of T3 and T4 were determined from standards in a calibration curve which was used to calculate the concentrations of enzymatically released T3 or T4.

VII:B—In Vitro Performance Studies of T3 Release by Various Enzymes

The enzymatic release of T3 from Lipidated, PEGylated and peptide conjugated iodothyronine is presented in Table 1 below.

TABLE 1

| Sample | Pronase | Pancreatin | Esterase | Pepsin | Lipase | Amidase |
|---|---|---|---|---|---|---|
| mPEG-Amine-T3 | 69.3 | 11.6 | 0.0 | 0.0 | nd | nd |
| C16T3 | 0.7 | 0.8 | 0.7 | 0.0 | 0.0 | 0.0 |
| C8T3(C8) | 2.9 | 0.7 | 0.0 | 0.9 | 0.0 | 0.0 |
| T3C8 | 8.3 | 6.1 | 1.4 | 2.1 | 2.2 | 1.4 |
| T3C16 | 1.1 | 4.3 | 2.3 | 1.0 | 1.3 | 1.2 |
| GMP polyT3 | 54.0 | 7.6 | 0.0 | 10.6 | nd | nd |

(nd: not determined)

Due to poor solubility of the fatty acylated T3 conjugates, the assays were repeated with the addition of 2.5% (by volume) DMSO. Results were identical.

The proteolytic release of T3 or T4 from cGMP poly-T3 (random), cGMP poly-T4 (random), AG1-269a (N-capped), and AG1-281a (C-capped) is presented in Table 2 below:

TABLE 2

| | | Percent Release | | | | | |
|---|---|---|---|---|---|---|---|
| | | Gastric Simulator | | Intestinal Simulator | | Pronase | |
| Conjugate | Polymer Type | T3 | T4 | T3 | T4 | T3 | T4 |
| CML-449/01-NR3 [cGMP poly-T3] | random | 18 | | 15 | | 70 | |
| CML-426/01-NR4 [cGMP poly-T4] | random | | 4.8 | | 8.3 | | 50 |
| AG1-269a | N-capped | 41 | | 6 | | 87 | |
| AG1-281a | C-capped | n/a | | n/a | | 82 | |

VII:C—Caco-2 Intestinal Cell Studies

The following discussion recites in vitro performance studies conducted with regard to a specific embodiments of the present invention. Although these performance studies describe specific embodiments of the present invention, it is not limited to these embodiments. Alternative embodiments and modifications which would still be encompassed by the invention may be made by those skilled in the art, particularly in light of the foregoing teachings. Therefore, this invention is intended to cover any alternative embodiments, modifications or equivalents which may be within the spirit and scope of the invention.

Monolayers of Caco-2 human intestinal epithelial cells are increasingly being used to predict the absorption of orally delivered drugs. We used the Caco-2 transwell system and other in vitro assays to evaluate the performance of Polythroid. Our findings indicated that polythroid enhances oral delivery of thyroid hormones for the treatment of hypothyroid disorders.

Caco-2 cells were grown on the surface of collagen coated wells in a 24 well format to form confluent monolayers that represented small segments of the intestine. The wells were removable and contained a top chamber representing the apical side (facing the lumen of the intestine) and a bottom chamber representing the basolateral side (site of serosal drug absorption). The integrity of the epithelial barrier was monitored by testing the electrical resistance across the monolayer. Absorption of drugs was studied by adding sample to the apical side and assaying the concentration of the drug in the basolateral chamber following incubation.

Polythroid is a synthetic polymer of glutamic acid with T4 and T3 covalently attached by a peptide bond linkage. The polymer may be formulated as the delivery vehicle for the thyroid hormones. In this embodiment of the present invention, the polymer was not designed to cross the intestinal barrier itself. Rather, this particular embodiment was designed to release T4 and T3 in a time dependent manner. Release of the thyroid hormones was dependent on the enzymatic cleavage of the glutamic acid polymer. The digestion of Polythroid and subsequent release of T4 resulted from encountering proteolytic enzymes produced by Caco-2 intestinal epithelial cells. Proteins are digested into small polypeptides by gastric pepsin and pancreatic enzymes secreted into the small intestine. Intestinal epithelial cells then function to further breakdown the small polypeptides. They accomplish this with proteolytic enzymes referred to as brush border proteases that are attached to the cell surface.

Monitoring the effect of brush border peptidases on Polythroid required development of an assay to specifically distinguish Polythroid from polyglutamic acid and the thyroid hormones. Therefore, we developed an enzyme-linked immunosorbent assay (ELISA) that specifically recognizes Polythroid. The assay employed antibodies against the glutamic acid polymer to capture Polythroid and antibodies to T4 or T3 to detect the presence of Polythroid. The assay had no cross-reactivity with polyglutamic acid or the thyroid hormones themselves. Consequently, proteolytic degradation of Polythroid resulted in T4 and T3 release from the polymer and a corresponding decrease in ELISA reactivity. The Polythroid specific ELISA was, therefore, used to monitor the breakdown of Polythroid.

The Polythroid specific assay was used to analyze in situ digestion of Polythroid in Caco-2 cell cultures. Different concentrations of Polythroid were added to the apical side of Caco-2 cells and incubated for 4 hours in PBS at 37° C. (n=4). The apical side Polythroid concentration was measured by Polythroid specific ELISA before and after the 4 hour incubation. The results of this measurement are shown in FIG. 7. At the relatively high concentration of 100 micrograms, 26% of Polythroid was degraded, whereas at a 10-fold lower concentration 84% of the Polythroid was degraded. When a concentration of 0.5 micrograms was added (closer to the concentrations that would be encountered by the intestine in a normal human dose) the amount of Polythroid remaining after 4 hours of incubation was below the limit of detection for the ELISA (10 ng) indicating essentially complete digestion. The loss of Polymer in the apical chamber was not due to absorption of Polythroid across the monolayer since the basolateral chamber contained no detectable Polythroid in any of the experiments (see below). In a preferred embodiment, the intestinal cells provide a mechanism which causes the decrease in Polythroid concentration on the apical side by enzymatic digestion, cellular uptake of Polythroid, or a combination thereof. In a more preferred embodiment, enzymatic digestion is responsible for essentially all of the decrease in Polythroid concentration on the apical side because, at the higher concentrations, it is difficult for cellular uptake to account for such a large difference in the remaining Polythroid.

Absorption of T4 was monitored in the Caco-2 transwell system (n=4). PolyT4 (10 micrograms) was added to the apical side of the transwells. T4 was added to the apical side at a concentration equal to the T4 content of PolyT4. A commercial ELISA for T4 was used to determine the level of T4 in the basolateral chamber following incubation for 4 hours at 37° C. The results of this study are presented in FIG. 8. A significantly higher amount of T4 was absorbed from PolyT4 as compared to Caco-2 cells incubated with the amount of T4 equivalent to that contained in the polymer.

Polythroid specific ELISA was used to measure the amount of polymer in the basolateral chamber after incubation with Polythroid at a high concentration (100 micrograms). After 4 hours incubation, samples (n=4) from the basolateral side showed no reactivity in the ELISA. The results of this study are presented in FIG. 9. The limit of detection for Polythroid is 10 ng, therefore, less than 1/10,000 of the Polythroid was absorbed. In a preferred embodiment, within the limits of ELISA detection, Polythroid does not cross the Caco-2 monolayer.

VII:D—Proteolytic Digestion and Release of Thyroid Hormones from Polymers

Pepsin secreted by the gastric mucosa is the only protease active in the acid conditions of the stomach. The pancreas secretes a number of proteolytic enzymes into the intestine which degrade proteins and polypeptides. In a preferred embodiment, these endogenous proteases participate in release of T4 and T3 from Polythroid as the polymer descends the intestinal tract.

Tests were conducted on Polythroid in the USP gastric simulator and the USP intestinal simulator and compared to levels of digestion for Polythroid synthesized by different methods. The samples of Polythroid varied in the position of thyroid hormone attachment. Samples were dissolved in gastric simulator buffer containing pepsin or in intestinal simulator buffer containing pancreatic enzyme extract (pancreatin) and incubated for 24 hours at 37° C. Following digestion, samples were analyzed by HPLC for the content of released monomeric T4 and T3. FIGS. 10 and 11 show the levels of T4 and T3 following digestion in the gastric and intestinal simulators. Release varied depending on the position of thyroid hormone attachment. Polythroid with T4 and T3 attached at the C-terminus (C-capped) showed the highest level of digestion. In contrast, Polythroid with N-terminal attachment (N-capped) showed no digestion in the gastric simulator and a relatively low amount of digestion in the intestinal simulator. Polythroid with random attachment showed only marginal digestion in the gastric simulator and moderate digestion in the intestinal simulator. In a preferred embodiment, the rate of thyroid hormone release from Polythroid varies depending on the method of synthesis. In this preferred embodiment, this variation provides a means of controlling (fine tuning) timed release of oral delivery. In another preferred embodiment, the rate of thyroid hormone release from Polythroid varies depending upon the position of the interspersed iodothyronine active agent or agents within the carrier peptide. In this preferred interspersed embodiment, the positional variation provides a means of controlling or fine tuning timed release of oral delivery.

In a preferred embodiment of the present invention, T4 and T3 are released from Polythroid by pancreatic and intestinal cell proteases. In this preferred embodiment, T4 and T3 released from Polythroid are absorbed across intestinal monolayers. Polythroid enhances absorption of T4 across intestinal epithelium in vitro. Polythroid itself does not cross the intestinal epithelial barrier in vitro. Finally, in this preferred embodiment, the kinetics of time release may be controlled by the method of Polythroid synthesis.

Although the present invention has been described in terms of specific embodiments, particularly with regard to the in vitro performance studies, it is not limited to these embodiments. Alternative embodiments and modifications which would still be encompassed by the invention may be made by those skilled in the art, particularly in light of the foregoing teachings. Therefore, this invention is intended to cover any alternative embodiments, modifications or equivalents which may be within the spirit and scope of the invention.

VIII: In Vivo Performance Studies

VIII:A—Materials and Methods of the In Vivo Performance Studies (i) Solid Dose Oral Delivery Compounds were tested in Sprague-dawley rats (~250 g). Defined doses were delivered as capsules containing. Serum was collected from rats at 2, 4, 6, 9, 12 and 24 hours after capsule delivery. Total serum T3 concentrations were deter-

TABLE 3

Estimated Percent Release of T3 by Protease from Various PolyT3 Compounds

| Sample | cGMP Poly T3 | N-Capped Dimer | N-Capped Trimer | C-Capped Dimer | C-Capped Trimer | 20-Mer | Flanked Trimer |
|---|---|---|---|---|---|---|---|
| Percent T3 Released[1] | 70 | 90 | 100 | 95 | 20 | 68 | 94 |

[1]Samples were treated with S. griseus protease for 24 hours at 37° C.

Table 3 shows the percent of T3 released from various PolyT3 glutamic acid compounds. In general, shorter polymers were better digested than longer polymers. The C-capped dimmer was an exception, since it was poorly digested despite its short length. The results with N-capped trimer show that T3 can be completely released from a polymer in vitro.

In a preferred embodiment of the present invention, covalent attachment of T4 and T3 to a polypeptide provide advantages to oral delivery for thyroid hormone replacement therapy. For example, proteolytic enzymes produced by the pancreas and intestinal epithelial cells release T4 and T3 from Polythroid. In this preferred embodiment, T4 and T3 are released in a time dependent manner as they descend the intestinal tract. Once released the hormones are absorbed across the intestinal epithelium in the Caco-2 cell model. Further, data from the in vitro intestinal epithelial model demonstrates that attachment of T4 to polymers of glutamic acid, in this embodiment, enhances absorption of the thyroid hormones. In a preferred embodiment, the enhanced absorption is obtained by providing a second mechanism of uptake and/or enhancing solubility of the hormones. Polythroid itself does not cross the intestinal epithelial barrier in the in vitro Caco-2 model. Thus, another advantage of the present invention is that any concerns about systemic effects of the polymer are minimized since it is not absorbed into the bloodstream.

mined by ELISA using a commercially available kit (Total Triiodothyronine (Total T3) ELISA KIT, product #1700, ALPHA DIAGNOSTIC, San Antonio, Tex.). Total serum T4 concentrations were determined by ELISA using a commercially available kit (Total Thyronine (Total T4) ELISA KIT, product #1100, ALPHA DIAGNOSTIC, San Antonio, Tex.).

(ii) Solution Dose Oral Delivery

Compounds were tested in Sprague-dawley rats (~250 g). Defined doses were delivered as oral solutions in 0.5% sodium bicarbonate buffer with T3 sodium salt containing 12 mcgT3/kg or iodothyronine composition containing the equivalent amount of T3. Rats were dosed immediately following 0 hour serum collection. Serum was collected from rats at 2, 4, 6, 9, 12 and 24 hours after capsule delivery. Total serum T3 concentrations were determined by ELISA using a commercially available kit (Total Triiodothyronine (total T3) ELISA KIT, product #1700, ALPHA DIAGNOSTIC, San Antonio, Tex.). Total serum T4 concentrations were determined by ELISA using a commercially available kit (Total Thyronine (Total T4) ELISA KIT, product #1100, ALPHA DIAGNOSTIC, San Antonio, Tex.).

VIII:B—In Vivo Performance Studies Results (i) Performance of Various T3-Glutamic Acid Polymers vs. T3 Sodium Salt as an Oral Solid Dose

TABLE 4

Estimated Total T3 Serum Concentration AUC's From Various Solid Dose PolyT3 Studies

| Study No. | T3 Na | cGMP Poly T3 | N-Capped Dimer | N-Capped Trimer | C-Capped Dimer | C-Capped Trimer | 20-Mer | Flanked Trimer |
|---|---|---|---|---|---|---|---|---|
| 11 | 15350 | | 15920[B] (104%) | 18910[1] (123%) | | | | |
| 12 | 15624 | | | | | | 10820 (69%) | |

TABLE 4-continued

Estimated Total T3 Serum Concentration AUC's From Various Solid Dose PolyT3 Studies

| Study No. | T3 Na | cGMP Poly T3 | N-Capped Dimer | N-Capped Trimer | C-Capped Dimer | C-Capped Trimer | 20-Mer | Flanked Trimer |
|---|---|---|---|---|---|---|---|---|
| 13 | 14942 | | | | 12102 (81%) | 13343 (89%) | | |
| 15 | 15899 | | | | | | | 9260 (58%) |
| 16 | 15884 | 11187 (70%) | | | | | | |
| 17[3] | 9982 | | | 10208 (102%) | | | | 5136 (51%) |

Notes:
AUCs are based on area under the serum concentration curve where y = 0.
(A)Values in parenthesis were obtained by dividing the total AUC for the various Poly T3 compounds by the total AUC for T3 sodium (the active control).
[1]When analyzed using the unpaired "T" test, the comparison of total AUC's for N-Capped Trimer vs. T3 sodium was significant vs. the N-capped Dimer and the N-capped Dimer vs. T3 sodium were not significant (p more than 0.05).

The small molecular weight iodothyronine compositions of the invention are better absorbed in vivo than the randomly dispersed copolymers of amino acids and iodothyronine active agent, particularly the capped compositions. Table 4 shows the relative AUC's of a variety of peptidic iodothyronine compositions. Of particular note is the 123% AUC of T3 N-capped trimer (T3-EE, lot no. CBI PIC 06 #2) relative to the reference T3 sodium.

The enhanced digestion kinetics and absorption in vivo of the small molecular weight capped iodothyronine composition is an important performance characteristic. In a more preferred embodiment, therefore, the capped iodothyronine composition comprises a blend of 3,3',5-triiodothyronine (T3) covalently attached to the N-terminus of a glutamic acid dimer and 3,3',5,5'-tetraiodothyronine (T4) covalently attached to the N-terminus of a glutamic acid dimer.

(ii) Performance of T3 N-Capped Trimer (T3-EE) vs. T3 Sodium Salt as an Oral Solution Dose.

TABLE 6

Mean Total Serum Concentrations and Delta of T3 Sodium Salt vs. T3 N-capped Trimer (T3-EE)

| | Total T3 serum levels | | Delta of total T3 serum levels[1] | |
|---|---|---|---|---|
| Hours | T3 sodium salt (ng/dL) | T3 N-capped trimer (ng/dL) | T3 sodium salt (ng/dL) | T3 N-capped trimer (ng/dL) |
| 0 | 117 +/− 20 | 130 +/− 30 | 0 | 0 |
| 2 | 251 +/− 29 | 371 +/− 25 | (+) 134 +/− 27 | (+) 241 +/− 36 |
| 4 | 209 +/− 49 | 314 +/− 35 | (+) 92 +/− 35 | (+) 184 +/− 53 |
| 6 | 187 +/− 26 | 256 +/− 58 | (+) 70 +/− 15 | (+) 126 +/− 85 |
| 9 | 194 +/− 40 | 208 +/− 41 | (+) 77 +/− 24 | (+) 78 +/− 70 |
| 12 | 156 +/− 22 | 197 +/− 28 | (+) 39 +/− 23 | (+) 67 +/− 57 |
| 24 | 162 +/− 54 | 169 +/− 51 | (+) 45 +/− 43 | (+) 39 +/− 75 |

[1]Change in total T3 serum levels from 0 hour level

TABLE 5

Total T3 Serum Levels of T3 Sodium Salt vs. T3 N-capped Trimer (T3-EE) Individual Animals

| | T3 sodium salt (ng/dL) | | | | | T3 N-capped trimer (ng/dL) | | | | |
|---|---|---|---|---|---|---|---|---|---|---|
| Hours | Rat #1 | Rat #2 | Rat #3 | Rat #4 | Rat #5 | Rat #1 | Rat #2 | Rat #3 | Rat #4 | Rat #5 |
| 0 | 108 | 143 | 91 | 115 | 128 | 82 | 133 | 142 | 128 | 165 |
| 2 | 242 | 298 | 250 | 246 | 220 | 374 | 392 | 339 | 353 | 398 |
| 4 | 179 | 295 | 182 | 191 | 198 | 358 | 275 | 297 | 296 | 343 |
| 6 | 191 | 225 | 153 | 190 | 177 | 356 | 206 | 250 | 239 | 230 |
| 9 | 175 | 223 | 133 | 204 | 233 | 281 | 191 | 189 | 197 | 182 |
| 12 | 150 | 184 | 147 | 171 | 127 | 242 | 189 | 201 | 182 | 170 |
| 24 | 161 | 255 | 138 | 129 | 128 | 232 | 151 | 213 | 129 | 119 |

TABLE 7

Mean Pharmacokinetic Parameters of T3 sodium salt vs. T3 N-capped Trimer (T3-EE)

|  | Cmax +/− SD (ng/dL) | Percent of T3 sodium salt | AUC[1] (0–24 h) +/− SD (ng h/dL) | Percent of T3 sodium salt | Delta @ Cmax[2] (ng/dL) | Percent of T3 sodium salt |
|---|---|---|---|---|---|---|
| T3 sodium salt | 251 +/− 29 | 100 | 1,425 +/− 448 | 100 | 137 +/− 22 | 100 |
| T3 N-capped Trimer (T3-EE) | 371 +/− 25 | 147.8 | 2,354 +/− 1,217 | 165.2 | 241 +/− 36 | 175.9 |

[1]Mean AUC (0–24) from lowest Y value of T3 serum concentrations
[2]Change in total T3 serum levels from 0 hour level Total T3 serum levels of individual animals (n=5) for T3 sodium salt and T3 N-capped trimer (T3-EE) are shown in Table 5. The mean total T3 serum values and mean Δ (change from zero hour level) serum levels of T3 sodium salt and T3 N-capped trimer (T3-EE) are shown in Table 6. Pharmacokinetic parameters are summarized in Table 7. FIG. 12 shows the mean serum concentration curves of T3 sodium salt vs. T3 N-capped trimer (T3-EE). FIG. 13 shows the mean delta serum concentration curves of T3 sodium salt vs. T3 N-capped trimer (T3-EE). The mean AUC for T3 N-capped trimer (T3-EE) was increased by 50.3 percent relative to the T3 sodium salt AUC. The Cmax of T3 N-capped trimer (T3-EE) was increased by 65.2 percent as compared to that of the T3 sodium salt. Similarly, the Δmax of T3 N-capped trimer (T3-EE) was increased by 75.9 percent relative to the Δmax T3 sodium salt. In conclusion, T3 absorption was substantially enhanced by the covalently bound glutamic acid peptide. In this example, the attached peptide clearly serves as an adjuvant for T3 absorption.

(iii) Performance of T3 N-Capped Trimer (T3-EE) vs. T3 Sodium Salt with and without the Presence of T4 Sodium Salt when Administered as an Oral Solution Dose.

Oral solution doses administered in this example were T3 sodium salt containing 18 mcg/kg of T3, T3 N-capped trimer containing 18 mcg/kg of T3, T3 sodium salt containing 18 mcg/kg of T3 plus T4 sodium salt containing 162 mcg/kg T4 (1:9 T3:T4 wt:wt ratio), and T3 N-capped trimer containing 18 mcg/kg of T3 plus T4 sodium salt containing 162 mcg/kg of T4 (1:9 T3:T4 wt:wt ratio).

TABLE 8

Total T3 serum concentrations of T3 sodium vs. T3 N-capped trimer Individual Rats

| | T3 sodium salt (ng/dL) | | | | | T3 N-capped trimer (ng/dL) | | | | |
|---|---|---|---|---|---|---|---|---|---|---|
| Hours | Rat #1 | Rat #2 | Rat #3 | Rat #4 | Rat #5 | Rat #1 | Rat #2 | Rat #3 | Rat #4 | Rat #5 |
| 0 | 255 | 268 | 199 | 134 | 148 | 182 | 170 | 253 | 165 | 128 |
| 2 | 670 | 303 | 448 | 441 | 410 | 654 | 993 | 842 | 600 | 704 |
| 4 | 711 | 402 | 578 | 414 | 372 | 617 | 992 | 866 | 651 | 449 |
| 6 | 615 | 464 | 440 | 244 | 328 | 590 | 678 | 668 | 458 | 381 |
| 9 | 367 | 305 | 293 | 223 | 247 | 422 | 355 | 333 | 280 | 338 |
| 12 | 341 | 427 | 298 | 180 | 197 | 412 | 460 | 375 | 288 | 237 |
| 24 | 241 | 255 | 172 | 114 | 89 | 211 | 249 | 275 | 143 | 138 |

TABLE 9

Total T3 serum concentrations of
T3 sodium plus T4 sodium vs. T3 N-capped trimer plus T4 sodium Individual Rats

| | T3 sodium salt plus T4 sodium | | | | | T3 N-capped trimer plus T4 sodium | | | | |
|---|---|---|---|---|---|---|---|---|---|---|
| Hours | Rat #1 | Rat #2 | Rat #3 | Rat #4 | Rat #5 | Rat #1 | Rat #2 | Rat #3 | Rat #4 | Rat #5 |
| 0 | 207 | 363 | 331 | 227 | 165 | 451 | 356 | 453 | 166 | 248 |
| 2 | 484 | 516 | 335 | 306 | 243 | 668 | 562 | 656 | 389 | 491 |
| 4 | 397 | 403 | 416 | 236 | 315 | 551 | 465 | 548 | 374 | 481 |
| 6 | 359 | 371 | 347 | 276 | 410 | 489 | 403 | 545 | 279 | 365 |
| 9 | 404 | 560 | 339 | 214 | 225 | 547 | 680 | 689 | 426 | 297 |
| 12 | 262 | 291 | 325 | 206 | 216 | 338 | 327 | 440 | 216 | 313 |
| 24 | 257 | 255 | 271 | 177 | 194 | 244 | 256 | 356 | 292 | 220 |

TABLE 10

Mean total T3 serum concentrations (ng/dL) of
T3 sodium vs. T3 N-capped trimer vs. T3 sodium
plus T4 sodium vs. T3 N-capped trimer plus T4 sodium

| Hours | T3 Sodium (ng/dL) | T3 N-cap Trimer (ng/dL) | T3 Sodium plus T4 Sodium (ng/dL) | T3 N-cap Trimer plus T4 Sodium (ng/dL) |
|---|---|---|---|---|
| 0 | 201 +/− 61 | 179 +/− 46 | 259 +/− 85 | 335 +/− 126 |
| 2 | 454 +/− 134 | 759 +/− 159 | 377 +/− 117 | 553 +/− 117 |
| 4 | 495 +/− 145 | 715 +/− 214 | 353 +/− 73 | 484 +/− 73 |
| 6 | 418 +/− 141 | 555 +/− 131 | 353 +/− 104 | 416 +/− 104 |
| 9 | 287 +/− 56 | 346 +/− 51 | 349 +/− 168 | 528 +/− 168 |
| 12 | 289 +/− 103 | 354 +/− 91 | 260 +/− 80 | 327 +/− 80 |
| 24 | 174 +/− 74 | 203 +/− 62 | 231 +/− 53 | 274 +/− 53 | serum levels are shown in Table 10. Pharmacokinetic parameters are summarized in Table 11. FIG. 14 shows the mean serum concentration curves. The Cmax of T3 N-capped trimer (T3-EE) was increased by 50.8 percent as compared to that of the T3 sodium salt. By comparison, the Cmax of T3 N-capped trimer (T3-EE) plus T4 sodium salt was increased 35.8 percent over that of T3 sodium salt plus T4 sodium salt. Δmax of T3 N-capped trimer (T3-EE) was increased by 85.6 percent relative to the Δmax of T3 sodium salt as compared to a 40.7 percent increase of T3 N-capped trimer (T3-EE) plus T4 sodium salt Δmax over that of T3 sodium salt plus T4 sodium salt. The mean AUC for T3 N-capped trimer (T3-EE) was increased by 72.1 percent relative to the T3 sodium salt AUC. Similarly, the mean AUC for T3 N-capped trimer (T3-EE) plus T4 sodium salt was increased by 73.8 percent relative to the T3 sodium salt plus T4 sodium salt AUC. In this example, T3 absorption was substantially decreased by the presence of T4 sodium salt. The attached carrier peptide of the T3 N-capped trimer,

TABLE 11

Pharmacokinetic parameters of
T3 sodium vs. T3 N-capped trimer vs. T3 sodium plus T4 sodium vs. T3 N-capped trimer plus T4 sodium

| Sample | Cmax +/− SD ng/dL | Percent T3 control | Deltamax[1] +/− SD (ng/dL) | Percent T3 control | AUC[2] +/− SD (ng h/dL) | Percent T3 control |
|---|---|---|---|---|---|---|
| T3 sodium | 513 +/− 108 | 100 | 320 +/− 101 | 100 | 3,036 +/− 643 | 100 |
| T3 N-cap Trimer | 774 +/− 151 | 150.8 | 594 +/− 141 | 185.6 | 5,224 +/− 1,532 | 172.1 |
| T3 sodium & T4 sodium | 435 +/− 94 | 100 | 177 +/− 91 | 100 | 1,821 +/− 696 | 100 |
| T3 N-cap Trimer & T4 sodium | 591 +/− 123 | 135.8 | 249 +/− 43 | 140.7 | 3,164 +/− 542 | 173.8 |

[1]Change in total T3 serum levels from 0 hour level
[2]Mean AUC (0–24) from lowest Y value of T3 serum concentrations Total T3 serum levels of individual animals (n=5) for T3 sodium salt, T3 N-capped trimer (T3-EE), T3 sodium salt plus T4 sodium salt (1:9 T3:T4 wt:wt ratio), and T3 N-capped trimer (T3-EE) plus T4 sodium salt (1:9 T3:T4 wt:wt ratio) are shown in Tables 8 and 9. The mean total T3 however, clearly served as an adjuvant for T3 absorption and partially eliminated the negative effect of T4 sodium salt on T3 bioavailability.

(iv) Performance of T4 N-Capped Trimer (T4-EE) vs. T4 Sodium Salt as Oral Solution Dose.

TABLE 12

Total T4 Serum Levels of T4 Sodium Salt vs. T4 N-capped Trimer (T4-EE) Individual Animals

| | T4 sodium salt (ng/dL) | | | | | T4 N-capped trimer (ng/dL) | | | | |
|---|---|---|---|---|---|---|---|---|---|---|
| Hours | Rat #1 | Rat #2 | Rat #3 | Rat #4 | Rat #5 | Rat #1 | Rat #2 | Rat #3 | Rat #4 | Rat #5 |
| 0 | 5.5 | 6.0 | 5.6 | 3.4 | 3.5 | 7.4 | 5.9 | 7.4 | 5.1 | 5.7 |
| 2 | 5.6 | 6.0 | 6.1 | 5.9 | 6.1 | 9.7 | 9.4 | 9.6 | 7.8 | 7.9 |
| 4 | 7.0 | 6.8 | 6.7 | 6.6 | 4.0 | 12.5 | 11.5 | 11.0 | 9.6 | 11.6 |
| 6 | 7.9 | 9.0 | 6.8 | 8.3 | 6.4 | 11.2 | 12.4 | 11.6 | 7.8 | 6.9 |
| 9 | 7.0 | 8.4 | 9.1 | 11.0 | 4.6 | 12.1 | 11.3 | 11.4 | 11.1 | 13.0 |
| 12 | 6.1 | 6.2 | 8.3 | 6.8 | 7.1 | 12.9 | 12.2 | 12.5 | 14.0 | 8.4 |
| 24 | 5.1 | 7.9 | 6.4 | 5.8 | 5.2 | 10.8 | 10.1 | 7.5 | 7.7 | 10.3 |

TABLE 13

Mean Total T4 Serum Concentrations and Mean Deltas of
T4 Sodium Salt vs. T4 N-capped Trimer (T4-EE)

| | Total T4 serum levels | | Delta of total T4 serum levels[1] | |
|---|---|---|---|---|
| Hours | T4 sodium salt (ng/dL) | T4 N-capped trimer (ng/dL) | T4 sodium salt (ng/dL) | T4 N-capped trimer (ng/dL) |
| 0 | 4.8 +/− 1.2 | 6.3 +/− 1.0 | 0 | 0 |
| 2 | 5.9 +/− 0.2 | 8.9 +/− 0.9 | (+) 1.1 +/− 1.3 | (+) 2.6 +/− 0.6 |
| 4 | 6.2 +/− 1.2 | 11.2 +/− 1.1 | (+) 1.4 +/− 1.1 | (+) 4.9 +/− 0.9 |
| 6 | 7.7 +/− 1.1 | 10.0 +/− 2.5 | (+) 2.9 +/− 1.3 | (+) 3.7 +/− 2.0 |
| 9 | 8.0 +/− 2.4 | 11.8 +/− 0.8 | (+) 3.2 +/− 2.6 | (+) 5.5 +/− 1.3 |
| 12 | 6.9 +/− 0.9 | 12.0 +/− 2.1 | (+) 2.1 +/− 1.6 | (+) 5.7 +/− 2.2 |
| 24 | 6.1 +/− 1.1 | 9.3 +/− 1.6 | (+) 1.3 +/− 1.1 | (+) 3.0 +/− 1.8 |

[1]Change in total T4 serum levels from 0 hour level

TABLE 14

Mean Pharmacokinetic Parameters of T4 sodium salt vs. T4 N-capped Trimer (T4-EE)

| | Cmax +/− SD (ng/dL) | Percent of T4 sodium salt | AUC[1] (0–24 h) +/−SD (ng h/dL) | Percent of T4 sodium salt | Delta @ Cmax[2] (ng/dL) | Percent of T4 sodium salt |
|---|---|---|---|---|---|---|
| T4 sodium salt | 8.8 +/− 1.5 | 100 | 47 +/− 25 | 100 | 4.0 +/− 2.1 | 100 |
| T4 N-capped Trimer (T4-EE) | 13.0 +/− 0.6 | 148 | 101 +/− 22 | 215 | 6.7 +/− 1.5 | 168 |

[1]Mean AUC (0–24) from lowest Y value of T4 serum concentrations
[2]Change in total T4 serum levels from 0 hour level Total T4 serum levels of individual animals (n=5) for T4 sodium salt and T4 N-capped trimer (T4-EE) are shown in Table 12. The mean total T4 serum values and mean Δ (change from zero hour level) serum levels of T4 sodium salt and T4 N-capped trimer (T4-EE) are shown in Table 13. Pharmacokinetic parameters are summarized in Table 14. FIG. 15 shows the mean serum concentration curves of T4 sodium salt vs. T4 N-capped trimer (T4-EE). FIG. 16 shows the mean delta serum concentration curves of T4 sodium salt vs. T4 N-capped trimer (T4-EE). The mean AUC for T4 N-capped trimer (T4-EE) was increased by 115 percent relative to the T4 sodium salt AUC. The Cmax of T4 N-capped trimer (T4-EE) was increased by 48 percent as compared to that of the T3 sodium salt. Similarly, the Δmax (Δ at Cmax) of T4 N-capped trimer (T4-EE) was increased by 68 percent relative to the Δmax of T4 sodium salt. In conclusion, T4 absorption was substantially enhanced by the covalently bound glutamic acid peptide. In this example, the attached peptide clearly serves as an adjuvant for T4 absorption. Additionally, the Tmax (time to reach maximal concentration) was increased from 8.4 hours for T4 sodium salt to 10.2 hours for T4 N-capped trimer (T4-EE) illustrating timed-release from the thyroid hormone conjugate.

IX: LC/MS Method

In order to test for the presence of dimers and trimers in rat serum after administration of Polythroid an analytical study was performed using a powerful technique referred to as LC/MS. Employing this method, dimers (T4-Glu and Glu-T4) were detectable at levels as low as 0.1 ng/mL and trimers (T4-Glu-Glu, Glu-T4-Glu and Glu-Glu-T4) were detectable at 0.25 to 0.5 ng/mL in spiked control sera. This sensitivity is more than adequate to determine whether significant absorption of small chain polymers occurs in the rat. The data from that study indicated that no detectable quantities of the dimers and trimers were observed.

What is claimed is:

1. A composition comprising:
   a single T3 conjugated to the N-terminus of a peptide carrier,
   wherein said peptide carrier is fewer than 15 amino acids and consists essentially of the one or more of the 20 naturally occurring amino acids; and
   wherein said composition is in a form suitable for oral administration and delivery of a pharmaceutically effective amount of T3.

2. The composition of claim 1, comprising T3-Glu-Glu.

3. The composition of claim 1, comprising T3-Ser-Ser.

4. The composition of claim 1, comprising T3-PolySer.

5. The composition of claim 1, comprising T3-Lys.

6. The composition of claim 1, wherein said carrier peptide is an amino acid.

7. The composition of claim 1, wherein said composition formulations afford sustained release of T3.

8. The composition of claim 1, wherein said carrier peptide enhances absorption.

9. The composition of claim 1, wherein said carrier peptide is a homopolymer.

10. The composition of claim 1, wherein said carrier peptide is a heteropolymer.

11. The composition of claim 1, which is formulated to enhance the solubility of the T3 in aqueous or organic solvents.

12. The composition of claim 11, wherein said enhanced solubility allows even dispersion in polymer formulations.

13. A method of treating a thyroid hormone disorder comprising administering the composition of claim 1.

14. The composition of claim 1, wherein said form suitable for oral administration is a tablet, a capsule, a suspension, or a solution.

15. The composition of claim 1, wherein said carrier peptide consists of one or more of the 20 naturally occurring amino acids.

16. A composition comprising a Glu-Glu carrier peptide that comprises at least one T3 active agent, with the proviso that no more than four T3 active agents are contiguously bonded.

17. T3-Glu-Glu.

18. A composition comprising T3-Glu-Glu.

19. The composition of claim 18, wherein said T3-Glu-Glu is covalently attached to PEG.

20. The composition of claim 18, wherein said T3-Glu-Glu is covalently attached to cyclodextrin.

21. The composition of claim 18, wherein said T3-Glu-Glu is non-covalently attached to cyclodextrin.

22. A method of treating a thyroid hormone disorder comprising administering the composition of claim 15.

23. A method of treating a thyroid hormone disorder comprising administering the composition of claim 16.

24. A method of treating a thyroid hormone disorder comprising administering T3-Glu-Glu.

25. A method of treating a thyroid hormone disorder comprising administering the composition of claim 18.

* * * * *